United States Patent [19]
Lindahl et al.

[11] Patent Number: 6,015,889
[45] Date of Patent: *Jan. 18, 2000

[54] PROTEIN RIB, A CELL SURFACE PROTEIN THAT CONFERS IMMUNITY TO MANY STRAINS OF THE GROUP B STREPTOCOCCUS: PROCESS FOR PURIFICATION OF THE PROTEIN, REAGENT KIT AND PHARMACEUTICAL COMPOSITION

[75] Inventors: Gunnar Lindahl; Margaretha Stalhammar-Carlemalm; Lars Stenberg, all of Lund, Sweden

[73] Assignee: Gunnar Lindahl, Lund, Sweden

[ * ] Notice: This patent is subject to a terminal disclaimer.

[21] Appl. No.: 08/904,263

[22] Filed: Jul. 31, 1997

Related U.S. Application Data

[63] Continuation-in-part of application No. 08/487,675, Jun. 7, 1995, Pat. No. 5,869,064, which is a continuation of application No. PCT/SE94/00246, Mar. 21, 1994.

[30] Foreign Application Priority Data

Mar. 19, 1993 [WO] WIPO ............... PCT/SE93/00234

[51] Int. Cl.[7] ................................................ C07H 21/04
[52] U.S. Cl. ................ 536/23.5; 536/117; 435/69.3; 435/101; 435/320.1; 424/244.1
[58] Field of Search ................... 536/23.7, 117, 536/123; 435/69.3, 101, 320.1; 424/244.1

[56] References Cited

U.S. PATENT DOCUMENTS

| | | | |
|---|---|---|---|
| 4,439,422 | 3/1984 | Swenson et al. | 424/92 |
| 5,648,241 | 7/1997 | Michel et al. | 435/69.3 |

FOREIGN PATENT DOCUMENTS

| | | |
|---|---|---|
| 0367890 | 5/1990 | European Pat. Off. |
| 9104049 | 4/1991 | WIPO . |
| 9217588 | 10/1992 | WIPO . |
| 9421685 | 9/1994 | WIPO . |

OTHER PUBLICATIONS

Lewin, Roger, Science, vol. 237, p. 1570, 1987.
Reeck et al. CCell, vol. 50, p. 667. Aug. 28, 1987.
Carberry–Goh et al., 1987, In:Streptococcal genetics, pp. 22–24.
Michel, J. L. et al., Proc. Nat'l, Acad. Sci, USA, vol. 89, Nov., pp. 10060–10064, 1992.
Russell–Jones, G. J. et al., J. Exp. Med, Nov., vol. 160, pp. 1467–1475, 1984.
Salasia, S.I.O. et al., APMIS, vol. 102, pp. 925–930, 1994.
Linden, ACTA path. microbiol. Immun. Scand. Sect. B, 91, pp. 145–151, 1983.
Lancefield, R. C. et al., J. of Exp. Med., vol. 142, pp. 165–179, 1975.
Michel, James et al, pp. 214–218, In:Genetics and Molecular Biology of Streptococci, Lactococci, and Enterococci, 1991.
Coppel et al., In Methods in Molecular Biology, vol. 21, Antibody Screening of expression Libraries, pp. 277–296.
Baker et al. J. Infect. Dis., Jul., vol. 154(1), pp. 47–54, 1986.
Baltimore, R.S. et al., J. of Immun., vol. 118(2), pp. 673–678, 1977.
Ferrieri, P., Reviews of Infect. Diseases, vol. 10, Supp. 2, Jul.–Aug., pp. S363–S366, 1988.

(List continued on next page.)

Primary Examiner—Christopher L. Chin
Assistant Examiner—Ginny Allen Portner
Attorney, Agent, or Firm—Birch, Stewart, Kolasch & Birch, LLP

[57] ABSTRACT

This invention relates to a new protein, designated Rib, and subfragments, multiples or variants thereof, which confers protective immunity against infection with many group B streptococcal strains, in particular those of serotype III. The invention includes a procedure for purification of the protein, a procedure for preparation of highly specific antibodies, a reagent kit, a DNA sequence encoding the protein and a pharmaceutical composition comprising the protein or fragments or variants thereof.

17 Claims, 14 Drawing Sheets

OTHER PUBLICATIONS

Westfelt et al., J. Biol. Chem. 271, 18892–18897 (Aug. 2, 1996).

Mukasa, H. et al., Infect. & Immun., vol. 7(4), pp. 578–585, 1973.

Carberry–Goh et al, 1987, In. Streptococcal Genetics, pp. 22–24.

Russel–Jones, G. J. et al, 1984, Nov., vol. 160, J. Exp. Medicine.

Sting, R. et al, J. of Chromatography, 1989, vol. 497, pp. 258–262 (German).

Talay, S. R. et al, 1991, Molecular Microbiology, vol. 5(7), pp. 1727–1734.

Linden, V. et al, 1983, ACTA Path. Microbiol, Immunol. Scand. Sect. B, vol. 91, pp. 153–156.

STAIN

BLOTS

Western blot analysis of 7 different λ clones.
Incubation with anti-Rib

Chromosomal Streptococcal DNA lane
1+8 λEcoRI/HindIII
2  BM110 DNA before CsCl 1μl
4  BM110 DNA after  CsCl 1μl
6  BM110 DNA Sau3AI       1μl λ Rib 3 DNA
(λ Maxi prep Promega)

lane
1 λEcoRI/HindIII
2 λRib 3
3 λRib 3 BamHI
4 λRib 3 SalI
5 λRib 3 PstI

Figure 7A

```
1     AATATTTGTTTTTAAAGCCTATACTTTACTATGTATAGAGCTATACAGAATAAAGTAAAGGAGAATATTATGTTT              75
                                                                          M  F          -54

76    AGAAGGTCTAAAAATAACAGTTATGATACTTTACAGACGAAACAACGGTTTTCAATTAAGAAGTTTAAGTTTGGT            150
      R  R  S  K  N  N  S  Y  D  T  L  Q  T  K  Q  R  F  S  I  K  K  F  K  F  G           -29

151   GCAGCTTCTGTACTAATTGGTATTAGTTTTTTAGGAGGTTTTACTCAAGGCAATTTAATATTCTACAGATACT             225
      A  A  S  V  L  I  G  I  S  F  L  G  G  F  T  Q  G  Q  F  N  I  S  T  D  T            -4

226   GTGTTTGCAGCTGAAGTAATTTCAGGAAGTGCTGTTACGTTAAACACAAATATGACTAAAAATGTTCAGAATGGT            300
      V  F  A  A  E  V  I  S  G  S  A  V  T  L  N  T  N  M  T  K  N  V  Q  N  G            22

301   AGAGCATATATAGATTTATAGATGTGAAAAATGGGAAAATAGATCCATTACAATTAATTACGTTAAATTCACCT             375
      R  A  Y  I  D  L  Y  D  V  K  N  G  K  I  D  P  L  Q  L  I  T  L  N  S  P            47

376   GATTTAAAAGCTCAGTATGTCATTAGGCAAGGCGGCAATTATTCACACAACCTTCTGAATTGACTACTGTTGGT            450
      D  L  K  A  Q  Y  V  I  R  Q  G  G  N  Y  F  T  Q  P  S  E  L  T  T  V  G            72

451   GCAGCTAGTATTAATTATACAGTATTGAAGACAGATGGAAGTCCTCATACGAAGCCTGATGGACAAGTGGATATT           525
      A  A  S  I  N  Y  T  V  L  K  T  D  G  S  P  H  T  K  P  D  G  Q  V  D  I            97

526   ATAAACGTTTCATTGACTATTTACAATTCTTCAGCTTTGAGAGATAAAATAGAAGTTAAAAAGAAAGCGGAA              600
      I  N  V  S  L  T  I  Y  N  S  S  A  L  R  D  K  I  D  E  V  K  K  K  A  E           122

601   GACCCTAAATGGGACGAGGGAAGTCGCGATAAAGTTTTAGATGATATCAAAACAGATATTGATAAT                   675
      D  P  K  W  D  E  G  S  R  D  K  V  L  I  S  L  D  D  I  K  T  D  I  D  N           147
```

Figure 7B

```
676  AATCCTAAGACGCAATCAGACATTGCCAATAAATCAGAAGTTACTAATTTAGAAAAAATACTAGTACCTCGA  750
148  N  P  K  T  Q  S  D  I  A  N  K  I  T  E  V  T  N  L  E  K  I  L  V  P  R     172

751  ATCCCA  756              GATGCCGATAAGAATGATCCAGCAGGTAAAGATCAGCAAGTCAATGTA
173  I  P     174  12 repeats: D  A  D  K  N  D  P  A  G  K  D  Q  Q  V  N  V GGTGAGACACCGGAAGGCAGAGAAGATTCTATTGGTAACTTACCAGATCTTCCGAAAGGTACAACAGTAGCCTTTGAA
     G  E  T  P  K  A  E  D  S  I  G  N  L  P  D  L  P  K  G  T  T  V  A  F  E ACTCCAGTTGATACGGCAACACCGGAGACAAACCAGCAAAAGTTGTTGTGACTTACCCAGATGGTTCAAAAGAT
     T  P  V  D  T  A  T  P  G  D  K  P  A  K  V  V  V  T  Y  P  D  G  S  K  D ACTGTAGATGTGACTGTTAAGGTTGTCGATCCACGTACA     3601 GATGCCGATAAG 3612
     T  V  D  V  T  V  K  V  V  D  P  R  T  partial repeat: 1123 D  A  D  K  1126

3613 AATGATCCAGCAGGTAAAGATCAGCAAGTCAAT 3646 GGTAAAGGAAATAAACTACCAGCACAGGTGAGAAT 3681
1127 N  D  P  A  G  K  D  Q  Q  V  N  1138 G  K  G  N  K  L  P  A  T  G  E  N  1149

3681 GCAACTCCATTCTTTAATGTGTAGCTTTGACAATTATGTCATCAGTTGGTTTATTATCTGTTTCTAAGAAAAAA 3756
1150 A  T  P  F  F  N  V  V  A  L  T  I  M  S  S  V  G  L  L  S  V  S  K  K  K     1174

3757 GAGGATTAATCTTTTGACCTAAAATGTCACTAAACTTTTCACCATTATTGGTGTGAACACATTAATAA         3825
1175 E  D                                                                          1176
```

```
Rib  -55  MFRRSKNNSYDTLQTKQRFSIKKFKFGAASVLIGISFLGGFTQGQFNIST          -6
          |||||||||||| |||||||||||||||||||||:||||.|||.:||  .
α    -56  MFRRSKNNSYDTSQTKQRFSIKKFKFGAASVLIGLSFLGGVTQGNLNIFE         -7

-5  DTVFAAEVISGSAVTLNTNMTKNVQNGRAYIDLYDVKNGKIDPLQLITLN         45
          :.:.||..|.|||.||||.:|||:|||.||||||||| ||||||||.|:
      -6  ESIVAASTIPGSAATLNTSITKNIQNGNAYIDLYDVKLGKIDPLQLIVLE         44

46  SPDLKAQYVIRQGGNYFTQPSELTTVGAASINYTVLKTDGSPHTKPDGQV         95
          .:.:.|.||:|||..|:..:.|:|  ..| ||:.|.:: .|| ||.|.|||:
      45  .QGFTAKYVFRQGTKYYGDVSQLQSTGRASLTYNIFGEDGLPHVKTDGQI         93

96  DIINVSLTIYNSSALRDKIDEVKKKAEDPKWDEGSRDKVLISLDDIKTDI        145
          ||:.|.||||:|..|||||:||...:|||||.|:||..||.:||.||||
      94  DIVSVALTIYDSTTLRDKIEEVRTNANDPKWTEESRTEVLTGLDTIKTDI        143

146  DNNPKTQSDIANKITEVTNLEKILVPRIP                              174
          |||||||.||..||.||.:|||:|||:||
     144  DNNPKTQTDIDSKIVEVNELEKLLVLS..                              170
```

12 or 9 repeats

```
     175  ..DADKNDPAGKDQQVNVGETPKAEDSIGNL...PDLPKGTTVAFETPVD
          ||  ||.|.:  |  ||  .:..|.:|   || .||........:...|
     171  VPDKDKYDPTGGETTVPQG.TPVSDKEITDLVKIPDGSKGVPTVVGDRPD
``` partial repeat

```
          TATPGDKPAKVVVTYPDGSKDTVDVTVKVVDPRT DADKNDPAGKDQQVN       1137
          |..|||...| ||||||.||||:|||.|...    | |||| |
          TNVPGDHKVTVEVTYPDGTKDTVEVTVHVTPKP  VPDKDKYDPTG           919

1138  GKGNKLPATGENATPFFNVVALTIMSSVGLLSVSKKKED                   1176
          ||||||||||||||||||||.||||:||||||||||||||
     920  KAQQVNGKGNKLPATGENATPFFNVAALTIISSVGLLSVSKKKED              964
```

FIG. 9A

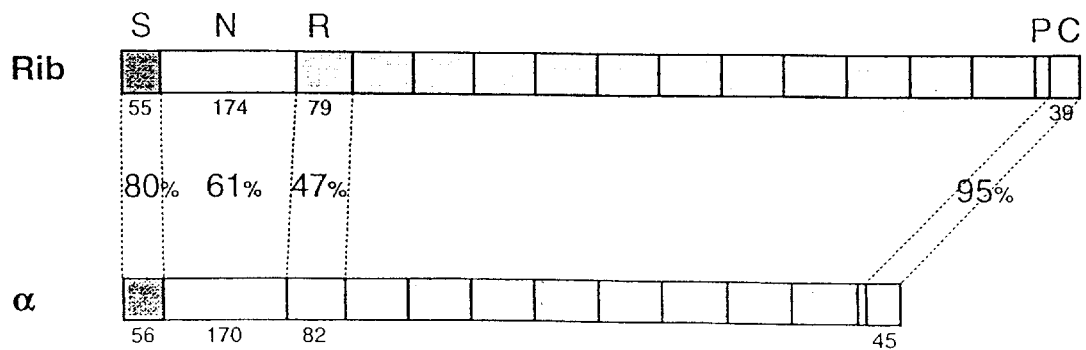

FIG. 9B

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
         (A) LENGTH: 12 amino acids
         (B) TYPE: amino acid
         (C) STRANDEDNESS: Not Relevant
         (D) TOPOLOGY: linear (ii) MOLECULE TYPE: peptide (ix) FEATURE:
         (A) NAME/KEY: CDS
         (B) LOCATION: 58..1929

(xi) SEQUENCE DESCRIPTION: SEQ ID NO:1:

Ala Glu Val Ile Ser Gly Asp Ala Val Thr Leu Asn
1               5                   10

(2) INFORMATION FOR SEQ ID NO:2:

(i) SEQUENCE CHARACTERISTICS:
         (A) LENGTH: 12 amino acids
         (B) TYPE: amino acid
         (C) STRANDEDNESS: Not Relevant
         (D) TOPOLOGY: linear (ii) MOLECULE TYPE: peptide (ix) FEATURE:
         (A) NAME/KEY: CDS
         (B) LOCATION: 1..921

(xi) SEQUENCE DESCRIPTION: SEQ ID NO:2:

Ala Glu Val Ile Ser Gly Ser Ala Val Thr Leu Asn
1               5                   10

(2) INFORMATION FOR SEQ ID NO:3:

(i) SEQUENCE CHARACTERISTICS:
         (A) LENGTH: 3825 base pairs
         (B) TYPE: nucleic acid
         (C) STRANDEDNESS: double
         (D) TOPOLOGY: linear (ii) MOLECULE TYPE: cDNA to mRNA (ix) FEATURE:
         (A) NAME/KEY: CDS
         (B) LOCATION: 70..3762

(xi) SEQUENCE DESCRIPTION: SEQ ID NO:3:

AATATTTGTT TTTAAAGCCT ATACTTTACT ATGTATAGAG CTATACAGAA TAAAGTAAAG          60

GAGAATATT ATG TTT AGA AGG TCT AAA AAT AAC AGT TAT GAT ACT TTA            108
          Met Phe Arg Arg Ser Lys Asn Asn Ser Tyr Asp Thr Leu
           1               5                  10

CAG ACG AAA CAA CGG TTT TCA ATT AAG AAG TTT AAG TTT GGT GCA GCT          156
Gln Thr Lys Gln Arg Phe Ser Ile Lys Lys Phe Lys Phe Gly Ala Ala
     15                  20                  25

TCT GTA CTA ATT GGT ATT AGT TTT TTA GGA GGT TTT ACT CAA GGG CAA          204
Ser Val Leu Ile Gly Ile Ser Phe Leu Gly Gly Phe Thr Gln Gly Gln
 30                  35                  40                  45

| | | |
|---|---|---|
| TTT AAT ATT TCT ACA GAT ACT GTG TTT GCA GCT GAA GTA ATT TCA GGA<br>Phe Asn Ile Ser Thr Asp Thr Val Phe Ala Ala Glu Val Ile Ser Gly<br>50 55 60 | 252 | |
| AGT GCT GTT ACG TTA AAC ACA AAT ATG ACT AAA AAT GTT CAG AAT GGT<br>Ser Ala Val Thr Leu Asn Thr Asn Met Thr Lys Asn Val Gln Asn Gly<br>65 70 75 | 300 | |
| AGA GCA TAT ATA GAT TTA TAT GAT GTG AAA AAT GGG AAA ATA GAT CCA<br>Arg Ala Tyr Ile Asp Leu Tyr Asp Val Lys Asn Gly Lys Ile Asp Pro<br>80 85 90 | 348 | |
| TTA CAA TTA ATT ACG TTA AAT TCA CCT GAT TTA AAA GCT CAG TAT GTC<br>Leu Gln Leu Ile Thr Leu Asn Ser Pro Asp Leu Lys Ala Gln Tyr Val<br>95 100 105 | 396 | |
| ATT AGG CAA GGC GGC AAT TAT TTC ACA CAA CCT TCT GAA TTG ACT ACT<br>Ile Arg Gln Gly Gly Asn Tyr Phe Thr Gln Pro Ser Glu Leu Thr Thr<br>110 115 120 125 | 444 | |
| GTT GGT GCA GCT AGT ATT AAT TAT ACA GTA TTG AAG ACA GAT GGA AGT<br>Val Gly Ala Ala Ser Ile Asn Tyr Thr Val Leu Lys Thr Asp Gly Ser<br>130 135 140 | 492 | |
| CCT CAT ACG AAG CCT GAT GGA CAA GTG GAT ATT ATA AAC GTT TCA TTG<br>Pro His Thr Lys Pro Asp Gly Gln Val Asp Ile Ile Asn Val Ser Leu<br>145 150 155 | 540 | |
| ACT ATT TAC AAT TCT TCA GCT TTG AGA GAT AAA ATA GAT GAA GTT AAA<br>Thr Ile Tyr Asn Ser Ser Ala Leu Arg Asp Lys Ile Asp Glu Val Lys<br>160 165 170 | 588 | |
| AAG AAA GCG GAA GAC CCT AAA TGG GAC GAG GGA AGT CGC GAT AAA GTT<br>Lys Lys Ala Glu Asp Pro Lys Trp Asp Glu Gly Ser Arg Asp Lys Val<br>175 180 185 | 636 | |
| TTG ATA AGT TTA GAT GAT ATC AAA ACA GAT ATT GAT AAT AAT CCT AAG<br>Leu Ile Ser Leu Asp Asp Ile Lys Thr Asp Ile Asp Asn Asn Pro Lys<br>190 195 200 205 | 684 | |
| ACG CAA TCA GAC ATT GCC AAT AAA ATA ACT GAA GTT ACT AAT TTA GAA<br>Thr Gln Ser Asp Ile Ala Asn Lys Ile Thr Glu Val Thr Asn Leu Glu<br>210 215 220 | 732 | |
| AAA ATA CTA GTA CCT CGA ATC CCA GAT GCC GAT AAG AAT GAT CCA GCA<br>Lys Ile Leu Val Pro Arg Ile Pro Asp Ala Asp Lys Asn Asp Pro Ala<br>225 230 235 | 780 | |
| GGT AAA GAT CAG CAA GTC AAT GTA GGT GAG ACA CCG AAG GCA GAA GAT<br>Gly Lys Asp Gln Gln Val Asn Val Gly Glu Thr Pro Lys Ala Glu Asp<br>240 245 250 | 828 | |
| TCT ATT GGT AAC TTA CCA GAT CTT CCG AAA GGT ACA ACA GTA GCC TTT<br>Ser Ile Gly Asn Leu Pro Asp Leu Pro Lys Gly Thr Thr Val Ala Phe<br>255 260 265 | 876 | |
| GAA ACT CCA GTT GAT ACG GCA ACA CCG GGA GAC AAA CCA GCA AAA GTT<br>Glu Thr Pro Val Asp Thr Ala Thr Pro Gly Asp Lys Pro Ala Lys Val<br>270 275 280 285 | 924 | |
| GTT GTG ACT TAC CCA GAT GGT TCA AAA GAT ACT GTA GAT GTG ACT GTT<br>Val Val Thr Tyr Pro Asp Gly Ser Lys Asp Thr Val Asp Val Thr Val<br>290 295 300 | 972 | |
| AAG GTT GTC GAT CCA CGT ACA GAT GCC GAT AAG AAT GAT CCA GCA GGT<br>Lys Val Val Asp Pro Arg Thr Asp Ala Asp Lys Asn Asp Pro Ala Gly<br>305 310 315 | 1020 | |
| AAA GAT CAG CAA GTC AAT GTA GGT GAG ACA CCG AAG GCA GAA GAT TCT<br>Lys Asp Gln Gln Val Asn Val Gly Glu Thr Pro Lys Ala Glu Asp Ser<br>320 325 330 | 1068 | |
| ATT GGT AAC TTA CCA GAT CTT CCG AAA GGT ACA ACA GTA GCC TTT GAA<br>Ile Gly Asn Leu Pro Asp Leu Pro Lys Gly Thr Thr Val Ala Phe Glu<br>335 340 345 | 1116 | |
| ACT CCA GTT GAT ACG GCA ACA CCG GGA GAC AAA CCA GCA AAA GTT GTT<br>Thr Pro Val Asp Thr Ala Thr Pro Gly Asp Lys Pro Ala Lys Val Val<br>350 355 360 365 | 1164 | |

```
GTG ACT TAC CCA GAT GGT TCA AAA GAT ACT GTA GAT GTG ACT GTT AAG              1212
Val Thr Tyr Pro Asp Gly Ser Lys Asp Thr Val Asp Val Thr Val Lys
            370                 375                 380

GTT GTC GAT CCG CGT ACA GAT GCC GAT AAG AAT GAT CCA GCA GGT AAA              1260
Val Val Asp Pro Arg Thr Asp Ala Asp Lys Asn Asp Pro Ala Gly Lys
        385                 390                 395

GAT CAG CAA GTC AAT GTA GGT GAG ACA CCG AAG GCA GAA GAT TCT ATT              1308
Asp Gln Gln Val Asn Val Gly Glu Thr Pro Lys Ala Glu Asp Ser Ile
                400                 405                 410

GGT AAC TTA CCA GAT CTT CCG AAA GGT ACA ACA GTA GCC TTT GAA ACT              1356
Gly Asn Leu Pro Asp Leu Pro Lys Gly Thr Thr Val Ala Phe Glu Thr
        415                 420                 425

CCA GTT GAT ACG GCA ACA CCG GGA GAC AAA CCA GCA AAA GTT GTT GTG              1404
Pro Val Asp Thr Ala Thr Pro Gly Asp Lys Pro Ala Lys Val Val Val
430                 435                 440                 445

ACT TAC CCA GAT GGT TCA AAA GAT ACT GTA GAT GTG ACT GTT AAG GTT              1452
Thr Tyr Pro Asp Gly Ser Lys Asp Thr Val Asp Val Thr Val Lys Val
                450                 455                 460

GTC GAT CCG CGT ACA GAT GCC GAT AAG AAT GAT CCA GCA GGT AAA GAT              1500
Val Asp Pro Arg Thr Asp Ala Asp Lys Asn Asp Pro Ala Gly Lys Asp
            465                 470                 475

CAG CAA GTC AAT GTA GGT GAG ACA CCG AAG GCA GAA GAT TCT ATT GGT              1548
Gln Gln Val Asn Val Gly Glu Thr Pro Lys Ala Glu Asp Ser Ile Gly
        480                 485                 490

AAC TTA CCA GAT CTT CCG AAA GGT ACA ACA GTA GCC TTT GAA ACT CCA              1596
Asn Leu Pro Asp Leu Pro Lys Gly Thr Thr Val Ala Phe Glu Thr Pro
    495                 500                 505

GTT GAT ACG GCA ACA CCG GGA GAC AAA CCA GCA AAA GTT GTT GTG ACT              1644
Val Asp Thr Ala Thr Pro Gly Asp Lys Pro Ala Lys Val Val Val Thr
510                 515                 520                 525

TAC CCA GAT GGT TCA AAA GAT ACT GTA GAT GTG ACT GTT AAG GTT GTC              1692
Tyr Pro Asp Gly Ser Lys Asp Thr Val Asp Val Thr Val Lys Val Val
            530                 535                 540

GAT CCG CGT ACA GAT GCC GAT AAG AAT GAT CCA GCA GGT AAA GAT CAG              1740
Asp Pro Arg Thr Asp Ala Asp Lys Asn Asp Pro Ala Gly Lys Asp Gln
        545                 550                 555

CAA GTC AAT GTA GGT GAG ACA CCG AAG GCA GAA GAT TCT ATT GGT AAC              1788
Gln Val Asn Val Gly Glu Thr Pro Lys Ala Glu Asp Ser Ile Gly Asn
    560                 565                 570

TTA CCA GAT CTT CCG AAA GGT ACA ACA GTA GCC TTT GAA ACT CCA GTT              1836
Leu Pro Asp Leu Pro Lys Gly Thr Thr Val Ala Phe Glu Thr Pro Val
575                 580                 585

GAT ACG GCA ACA CCG GGA GAC AAA CCA GCA AAA GTT GTT GTG ACT TAC              1884
Asp Thr Ala Thr Pro Gly Asp Lys Pro Ala Lys Val Val Val Thr Tyr
        590                 595                 600                 605

CCA GAT GGT TCA AAA GAT ACT GTA GAT GTG ACT GTT AAG GTT GTC GAT              1932
Pro Asp Gly Ser Lys Asp Thr Val Asp Val Thr Val Lys Val Val Asp
            610                 615                 620

CCG CGT ACA GAT GCC GAT AAG AAT GAT CCA GCA GGT AAA GAT CAG CAA              1980
Pro Arg Thr Asp Ala Asp Lys Asn Asp Pro Ala Gly Lys Asp Gln Gln
        625                 630                 635

GTC AAT GTA GGT GAG ACA CCG AAG GCA GAA GAT TCT ATT GGT AAC TTA              2028
Val Asn Val Gly Glu Thr Pro Lys Ala Glu Asp Ser Ile Gly Asn Leu
    640                 645                 650

CCA GAT CTT CCG AAA GGT ACA ACA GTA GCC TTT GAA ACT CCA GTT GAT              2076
Pro Asp Leu Pro Lys Gly Thr Thr Val Ala Phe Glu Thr Pro Val Asp
655                 660                 665

ACG GCA ACA CCG GGA GAC AAA CCA GCA AAA GTT GTT GTG ACT TAC CCA              2124
Thr Ala Thr Pro Gly Asp Lys Pro Ala Lys Val Val Val Thr Tyr Pro
        670                 675                 680                 685
```

-continued

| | | |
|---|---|---|
| GAT GGT TCA AAA GAT ACT GTA GAT GTG ACT GTT AAG GTT GTC GAT CCG<br>Asp Gly Ser Lys Asp Thr Val Asp Val Thr Val Lys Val Val Asp Pro<br>            690                    695                      700 | 2172 |
| CGT ACA GAT GCC GAT AAG AAT GAT CCA GCA GGT AAA GAT CAG CAA GTC<br>Arg Thr Asp Ala Asp Lys Asn Asp Pro Ala Gly Lys Asp Gln Gln Val<br>          705                    710                    715 | 2220 |
| AAT GTA GGT GAG ACA CCG AAG GCA GAA GAT TCT ATT GGT AAC TTA CCA<br>Asn Val Gly Glu Thr Pro Lys Ala Glu Asp Ser Ile Gly Asn Leu Pro<br>      720                    725                    730 | 2268 |
| GAT CTT CCG AAA GGT ACA ACA GTA GCC TTT GAA ACT CCA GTT GAT ACG<br>Asp Leu Pro Lys Gly Thr Thr Val Ala Phe Glu Thr Pro Val Asp Thr<br>      735                    740                    745 | 2316 |
| GCA ACA CCG GGA GAC AAA CCA GCA AAA GTT GTT GTG ACT TAC CCA GAT<br>Ala Thr Pro Gly Asp Lys Pro Ala Lys Val Val Val Thr Tyr Pro Asp<br>750                    755                    760                    765 | 2364 |
| GGT TCA AAA GAT ACT GTA GAT GTG ACT GTT AAG GTT GTC GAT CCG CGT<br>Gly Ser Lys Asp Thr Val Asp Val Thr Val Lys Val Val Asp Pro Arg<br>                    770                    775                    780 | 2412 |
| ACA GAT GCC GAT AAG AAT GAT CCA GCA GGT AAA GAT CAG CAA GTC AAT<br>Thr Asp Ala Asp Lys Asn Asp Pro Ala Gly Lys Asp Gln Gln Val Asn<br>                785                    790                    795 | 2460 |
| GTA GGT GAG ACA CCG AAG GCA GAA GAT TCT ATT GGT AAC TTA CCA GAT<br>Val Gly Glu Thr Pro Lys Ala Glu Asp Ser Ile Gly Asn Leu Pro Asp<br>         800                    805                    810 | 2508 |
| CTT CCG AAA GGT ACA ACA GTA GCC TTT GAA ACT CCA GTT GAT ACG GCA<br>Leu Pro Lys Gly Thr Thr Val Ala Phe Glu Thr Pro Val Asp Thr Ala<br>      815                    820                    825 | 2556 |
| ACA CCG GGA GAC AAA CCA GCA AAA GTT GTT GTG ACT TAC CCA GAT GGT<br>Thr Pro Gly Asp Lys Pro Ala Lys Val Val Val Thr Tyr Pro Asp Gly<br>830                    835                    840                    845 | 2604 |
| TCA AAA GAT ACT GTA GAT GTG ACT GTT AAG GTT GTC GAT CCG CGT ACA<br>Ser Lys Asp Thr Val Asp Val Thr Val Lys Val Val Asp Pro Arg Thr<br>                    850                    855                    860 | 2652 |
| GAT GCC GAT AAG AAT GAT CCA GCA GGT AAA GAT CAG CAA GTC AAT GTA<br>Asp Ala Asp Lys Asn Asp Pro Ala Gly Lys Asp Gln Gln Val Asn Val<br>                865                    870                    875 | 2700 |
| GGT GAG ACA CCG AAG GCA GAA GAT TCT ATT GGT AAC TTA CCA GAT CTT<br>Gly Glu Thr Pro Lys Ala Glu Asp Ser Ile Gly Asn Leu Pro Asp Leu<br>         880                    885                    890 | 2748 |
| CCG AAA GGT ACA ACA GTA GCC TTT GAA ACT CCA GTT GAT ACG GCA ACA<br>Pro Lys Gly Thr Thr Val Ala Phe Glu Thr Pro Val Asp Thr Ala Thr<br>      895                    900                    905 | 2796 |
| CCG GGA GAC AAA CCA GCA AAA GTT GTT GTG ACT TAC CCA GAT GGT TCA<br>Pro Gly Asp Lys Pro Ala Lys Val Val Val Thr Tyr Pro Asp Gly Ser<br>910                    915                    920                    925 | 2844 |
| AAA GAT ACT GTA GAT GTG ACT GTT AAG GTT GTC GAT CCG CGT ACA GAT<br>Lys Asp Thr Val Asp Val Thr Val Lys Val Val Asp Pro Arg Thr Asp<br>                    930                    935                    940 | 2892 |
| GCC GAT AAG AAT GAT CCA GCA GGT AAA GAT CAG CAA GTC AAT GTA GGT<br>Ala Asp Lys Asn Asp Pro Ala Gly Lys Asp Gln Gln Val Asn Val Gly<br>                945                    950                    955 | 2940 |
| GAG ACA CCG AAG GCA GAA GAT TCT ATT GGT AAC TTA CCA GAT CTT CCG<br>Glu Thr Pro Lys Ala Glu Asp Ser Ile Gly Asn Leu Pro Asp Leu Pro<br>         960                    965                    970 | 2988 |
| AAA GGT ACA ACA GTA GCC TTT GAA ACT CCA GTT GAT ACG GCA ACA CCG<br>Lys Gly Thr Thr Val Ala Phe Glu Thr Pro Val Asp Thr Ala Thr Pro<br>      975                    980                    985 | 3036 |
| GGA GAC AAA CCA GCA AAA GTT GTT GTG ACT TAC CCA GAT GGT TCA AAA<br>Gly Asp Lys Pro Ala Lys Val Val Val Thr Tyr Pro Asp Gly Ser Lys<br>990                    995                  1000                1005 | 3084 |

```
GAT ACT GTA GAT GTG ACT GTT AAG GTT GTC GAT CCG CGT ACA GAT GCC    3132
Asp Thr Val Asp Val Thr Val Lys Val Val Asp Pro Arg Thr Asp Ala
            1010                1015                1020

GAT AAG AAT GAT CCA GCA GGT AAA GAT CAG CAA GTC AAT GTA GGT GAG    3180
Asp Lys Asn Asp Pro Ala Gly Lys Asp Gln Gln Val Asn Val Gly Glu
        1025                1030                1035

ACA CCG AAG GCA GAA GAT TCT ATT GGT AAC TTA CCA GAT CTT CCG AAA    3228
Thr Pro Lys Ala Glu Asp Ser Ile Gly Asn Leu Pro Asp Leu Pro Lys
        1040                1045                1050

GGT ACA ACA GTA GCC TTT GAA ACT CCA GTT GAT ACG GCA ACA CCG GGA    3276
Gly Thr Thr Val Ala Phe Glu Thr Pro Val Asp Thr Ala Thr Pro Gly
        1055                1060                1065

GAC AAA CCA GCA AAA GTT GTT GTG ACT TAC CCA GAT GGT TCA AAA GAT    3324
Asp Lys Pro Ala Lys Val Val Val Thr Tyr Pro Asp Gly Ser Lys Asp
1070            1075                1080                1085

ACT GTA GAT GTG ACT GTT AAG GTT GTC GAT CCG CGT ACA GAT GCC GAT    3372
Thr Val Asp Val Thr Val Lys Val Val Asp Pro Arg Thr Asp Ala Asp
            1090                1095                1100

AAG AAT GAT CCA GCA GGT AAA GAT CAG CAA GTC AAT GTA GGT GAG ACA    3420
Lys Asn Asp Pro Ala Gly Lys Asp Gln Gln Val Asn Val Gly Glu Thr
        1105                1110                1115

CCG AAG GCA GAA GAT TCT ATT GGT AAC TTA CCA GAT CTT CCG AAA GGT    3468
Pro Lys Ala Glu Asp Ser Ile Gly Asn Leu Pro Asp Leu Pro Lys Gly
        1120                1125                1130

ACA ACA GTA GCC TTT GAA ACT CCA GTT GAT ACG GCA ACA CCG GGA GAC    3516
Thr Thr Val Ala Phe Glu Thr Pro Val Asp Thr Ala Thr Pro Gly Asp
        1135                1140                1145

AAA CCA GCA AAA GTT GTT GTG ACT TAC CCA GAT GGT TCA AAA GAT ACT    3564
Lys Pro Ala Lys Val Val Val Thr Tyr Pro Asp Gly Ser Lys Asp Thr
1150            1155                1160                1165

GTA GAT GTG ACT GTT AAG GTT GTC GAT CCG CGT ACA GAT GCC GAT AAG    3612
Val Asp Val Thr Val Lys Val Val Asp Pro Arg Thr Asp Ala Asp Lys
            1170                1175                1180

AAT GAT CCA GCA GGT AAA GAT CAG CAA GTC AAT GGT AAA GGA AAT AAA    3660
Asn Asp Pro Ala Gly Lys Asp Gln Gln Val Asn Gly Lys Gly Asn Lys
        1185                1190                1195

CTA CCA GCA ACA GGT GAG AAT GCA ACT CCA TTC TTT AAT GTT GTA GCT    3708
Leu Pro Ala Thr Gly Glu Asn Ala Thr Pro Phe Phe Asn Val Val Ala
        1200                1205                1210

TTG ACA ATT ATG TCA TCA GTT GGT TTA TTA TCT GTT TCT AAG AAA AAA    3756
Leu Thr Ile Met Ser Ser Val Gly Leu Leu Ser Val Ser Lys Lys Lys
        1215                1220                1225

GAG GAT TAATCTTTTG ACCTAAAATG TCACTAAACT TTTCACCATT TATTGGTGTG      3812
Glu Asp
1230

AACACATTAA TAA                                                      3825

(2) INFORMATION FOR SEQ ID NO:4:

(i) SEQUENCE CHARACTERISTICS:
        (A) LENGTH: 1231 amino acids
        (B) TYPE: amino acid
        (D) TOPOLOGY: linear (ii) MOLECULE TYPE: protein (xi) SEQUENCE DESCRIPTION: SEQ ID NO:4:

Met Phe Arg Arg Ser Lys Asn Asn Ser Tyr Asp Thr Leu Gln Thr Lys
  1               5                  10                  15

Gln Arg Phe Ser Ile Lys Lys Phe Lys Phe Gly Ala Ala Ser Val Leu
            20                  25                  30
```

-continued

```
Ile Gly Ile Ser Phe Leu Gly Gly Phe Thr Gln Gly Gln Phe Asn Ile
         35                  40                  45

Ser Thr Asp Thr Val Phe Ala Ala Glu Val Ile Ser Gly Ser Ala Val
 50                  55                  60

Thr Leu Asn Thr Asn Met Thr Lys Asn Val Gln Asn Gly Arg Ala Tyr
 65                  70                  75                  80

Ile Asp Leu Tyr Asp Val Lys Asn Gly Lys Ile Asp Pro Leu Gln Leu
                 85                  90                  95

Ile Thr Leu Asn Ser Pro Asp Leu Lys Ala Gln Tyr Val Ile Arg Gln
                100                 105                 110

Gly Gly Asn Tyr Phe Thr Gln Pro Ser Glu Leu Thr Val Gly Ala
        115                 120                 125

Ala Ser Ile Asn Tyr Thr Val Leu Lys Thr Asp Gly Ser Pro His Thr
130                 135                 140

Lys Pro Asp Gly Gln Val Asp Ile Ile Asn Val Ser Leu Thr Ile Tyr
145                 150                 155                 160

Asn Ser Ser Ala Leu Arg Asp Lys Ile Asp Glu Val Lys Lys Lys Ala
                165                 170                 175

Glu Asp Pro Lys Trp Asp Glu Gly Ser Arg Asp Lys Val Leu Ile Ser
                180                 185                 190

Leu Asp Asp Ile Lys Thr Asp Ile Asp Asn Asn Pro Lys Thr Gln Ser
195                 200                 205

Asp Ile Ala Asn Lys Ile Thr Glu Val Thr Asn Leu Glu Lys Ile Leu
210                 215                 220

Val Pro Arg Ile Pro Asp Ala Asp Lys Asn Asp Pro Ala Gly Lys Asp
225                 230                 235                 240

Gln Gln Val Asn Val Gly Glu Thr Pro Lys Ala Glu Asp Ser Ile Gly
                245                 250                 255

Asn Leu Pro Asp Leu Pro Lys Gly Thr Thr Val Ala Phe Glu Thr Pro
                260                 265                 270

Val Asp Thr Ala Thr Pro Gly Asp Lys Pro Ala Lys Val Val Val Thr
                275                 280                 285

Tyr Pro Asp Gly Ser Lys Asp Thr Val Asp Val Thr Val Lys Val Val
                290                 295                 300

Asp Pro Arg Thr Asp Ala Asp Lys Asn Asp Pro Ala Gly Lys Asp Gln
305                 310                 315                 320

Gln Val Asn Val Gly Glu Thr Pro Lys Ala Glu Asp Ser Ile Gly Asn
                325                 330                 335

Leu Pro Asp Leu Pro Lys Gly Thr Thr Val Ala Phe Glu Thr Pro Val
                340                 345                 350

Asp Thr Ala Thr Pro Gly Asp Lys Pro Ala Lys Val Val Val Thr Tyr
                355                 360                 365

Pro Asp Gly Ser Lys Asp Thr Val Asp Val Thr Val Lys Val Val Asp
370                 375                 380

Pro Arg Thr Asp Ala Asp Lys Asn Asp Pro Ala Gly Lys Asp Gln Gln
385                 390                 395                 400

Val Asn Val Gly Glu Thr Pro Lys Ala Glu Asp Ser Ile Gly Asn Leu
                405                 410                 415

Pro Asp Leu Pro Lys Gly Thr Thr Val Ala Phe Glu Thr Pro Val Asp
                420                 425                 430

Thr Ala Thr Pro Gly Asp Lys Pro Ala Lys Val Val Val Thr Tyr Pro
                435                 440                 445

Asp Gly Ser Lys Asp Thr Val Asp Val Thr Val Lys Val Val Asp Pro
450                 455                 460
```

```
Arg Thr Asp Ala Asp Lys Asn Asp Pro Ala Gly Lys Asp Gln Gln Val
465                 470                 475                 480

Asn Val Gly Glu Thr Pro Lys Ala Glu Asp Ser Ile Gly Asn Leu Pro
            485                 490                 495

Asp Leu Pro Lys Gly Thr Thr Val Ala Phe Glu Thr Pro Val Asp Thr
            500                 505                 510

Ala Thr Pro Gly Asp Lys Pro Ala Lys Val Val Val Thr Tyr Pro Asp
            515                 520                 525

Gly Ser Lys Asp Thr Val Asp Val Thr Val Lys Val Val Asp Pro Arg
530                 535                 540

Thr Asp Ala Asp Lys Asn Asp Pro Ala Gly Lys Asp Gln Gln Val Asn
545                 550                 555                 560

Val Gly Glu Thr Pro Lys Ala Glu Asp Ser Ile Gly Asn Leu Pro Asp
            565                 570                 575

Leu Pro Lys Gly Thr Thr Val Ala Phe Glu Thr Pro Val Asp Thr Ala
            580                 585                 590

Thr Pro Gly Asp Lys Pro Ala Lys Val Val Val Thr Tyr Pro Asp Gly
            595                 600                 605

Ser Lys Asp Thr Val Asp Val Thr Val Lys Val Val Asp Pro Arg Thr
610                 615                 620

Asp Ala Asp Lys Asn Asp Pro Ala Gly Lys Asp Gln Gln Val Asn Val
625                 630                 635                 640

Gly Glu Thr Pro Lys Ala Glu Asp Ser Ile Gly Asn Leu Pro Asp Leu
            645                 650                 655

Pro Lys Gly Thr Thr Val Ala Phe Glu Thr Pro Val Asp Thr Ala Thr
            660                 665                 670

Pro Gly Asp Lys Pro Ala Lys Val Val Val Thr Tyr Pro Asp Gly Ser
            675                 680                 685

Lys Asp Thr Val Asp Val Thr Val Lys Val Val Asp Pro Arg Thr Asp
690                 695                 700

Ala Asp Lys Asn Asp Pro Ala Gly Lys Asp Gln Gln Val Asn Val Gly
705                 710                 715                 720

Glu Thr Pro Lys Ala Glu Asp Ser Ile Gly Asn Leu Pro Asp Leu Pro
            725                 730                 735

Lys Gly Thr Thr Val Ala Phe Glu Thr Pro Val Asp Thr Ala Thr Pro
            740                 745                 750

Gly Asp Lys Pro Ala Lys Val Val Val Thr Tyr Pro Asp Gly Ser Lys
            755                 760                 765

Asp Thr Val Asp Val Thr Val Lys Val Val Asp Pro Arg Thr Asp Ala
770                 775                 780

Asp Lys Asn Asp Pro Ala Gly Lys Asp Gln Gln Val Asn Val Gly Glu
785                 790                 795                 800

Thr Pro Lys Ala Glu Asp Ser Ile Gly Asn Leu Pro Asp Leu Pro Lys
            805                 810                 815

Gly Thr Thr Val Ala Phe Glu Thr Pro Val Asp Thr Ala Thr Pro Gly
            820                 825                 830

Asp Lys Pro Ala Lys Val Val Thr Tyr Pro Asp Gly Ser Lys Asp
            835                 840                 845

Thr Val Asp Val Thr Val Lys Val Val Asp Pro Arg Thr Asp Ala Asp
850                 855                 860

Lys Asn Asp Pro Ala Gly Lys Asp Gln Gln Val Asn Val Gly Glu Thr
865                 870                 875                 880
```

-continued

```
Pro Lys Ala Glu Asp Ser Ile Gly Asn Leu Pro Asp Leu Pro Lys Gly
                885                 890                 895

Thr Thr Val Ala Phe Glu Thr Pro Val Asp Thr Ala Thr Pro Gly Asp
            900                 905                 910

Lys Pro Ala Lys Val Val Thr Tyr Pro Asp Gly Ser Lys Asp Thr
        915                 920                 925

Val Asp Val Thr Val Lys Val Val Asp Pro Arg Thr Asp Ala Asp Lys
    930                 935                 940

Asn Asp Pro Ala Gly Lys Asp Gln Gln Val Asn Val Gly Glu Thr Pro
945                 950                 955                 960

Lys Ala Glu Asp Ser Ile Gly Asn Leu Pro Asp Leu Pro Lys Gly Thr
                965                 970                 975

Thr Val Ala Phe Glu Thr Pro Val Asp Thr Ala Thr Pro Gly Asp Lys
            980                 985                 990

Pro Ala Lys Val Val Val Thr Tyr Pro Asp Gly Ser Lys Asp Thr Val
        995                 1000                1005

Asp Val Thr Val Lys Val Val Asp Pro Arg Thr Asp Ala Asp Lys Asn
    1010                1015                1020

Asp Pro Ala Gly Lys Asp Gln Gln Val Asn Val Gly Glu Thr Pro Lys
1025                1030                1035                1040

Ala Glu Asp Ser Ile Gly Asn Leu Pro Asp Leu Pro Lys Gly Thr Thr
                1045                1050                1055

Val Ala Phe Glu Thr Pro Val Asp Thr Ala Thr Pro Gly Asp Lys Pro
            1060                1065                1070

Ala Lys Val Val Val Thr Tyr Pro Asp Gly Ser Lys Asp Thr Val Asp
        1075                1080                1085

Val Thr Val Lys Val Val Asp Pro Arg Thr Asp Ala Asp Lys Asn Asp
    1090                1095                1100

Pro Ala Gly Lys Asp Gln Gln Val Asn Val Gly Glu Thr Pro Lys Ala
1105                1110                1115                1120

Glu Asp Ser Ile Gly Asn Leu Pro Asp Leu Pro Lys Gly Thr Thr Val
                1125                1130                1135

Ala Phe Glu Thr Pro Val Asp Thr Ala Thr Pro Gly Asp Lys Pro Ala
            1140                1145                1150

Lys Val Val Val Thr Tyr Pro Asp Gly Ser Lys Asp Thr Val Asp Val
        1155                1160                1165

Thr Val Lys Val Val Asp Pro Arg Thr Asp Ala Asp Lys Asn Asp Pro
    1170                1175                1180

Ala Gly Lys Asp Gln Gln Val Asn Gly Lys Gly Asn Lys Leu Pro Ala
1185                1190                1195                1200

Thr Gly Glu Asn Ala Thr Pro Phe Phe Asn Val Val Ala Leu Thr Ile
                1205                1210                1215

Met Ser Ser Val Gly Leu Leu Ser Val Ser Lys Lys Lys Glu Asp
                1220                1225                1230

(2) INFORMATION FOR SEQ ID NO:5:

(i) SEQUENCE CHARACTERISTICS:
        (A) LENGTH: 237 base pairs
        (B) TYPE: nucleic acid
        (C) STRANDEDNESS: double
        (D) TOPOLOGY: linear (ii) MOLECULE TYPE: cDNA to mRNA (ix) FEATURE:
        (A) NAME/KEY: CDS
        (B) LOCATION: 1..237
```

(xi) SEQUENCE DESCRIPTION: SEQ ID NO:5:

```
GAT GCC GAT AAG AAT GAT CCA GCA GGT AAA GAT CAG CAA GTC AAT GTA         48
Asp Ala Asp Lys Asn Asp Pro Ala Gly Lys Asp Gln Gln Val Asn Val
            1235                1240                1245

GGT GAG ACA CCG AAG GCA GAA GAT TCT ATT GGT AAC TTA CCA GAT CTT         96
Gly Glu Thr Pro Lys Ala Glu Asp Ser Ile Gly Asn Leu Pro Asp Leu
        1250                1255                1260

CCG AAA GGT ACA ACA GTA GCC TTT GAA ACT CCA GTT GAT ACG GCA ACA        144
Pro Lys Gly Thr Thr Val Ala Phe Glu Thr Pro Val Asp Thr Ala Thr
        1265                1270                1275

CCG GGA GAC AAA CCA GCA AAA GTT GTT GTG ACT TAC CCA GAT GGT TCA        192
Pro Gly Asp Lys Pro Ala Lys Val Val Val Thr Tyr Pro Asp Gly Ser
1280                1285                1290                1295

AAA GAT ACT GTA GAT GTG ACT GTT AAG GTT GTC GAT CCA CGT ACA            237
Lys Asp Thr Val Asp Val Thr Val Lys Val Val Asp Pro Arg Thr
                1300                1305                1310
```

(2) INFORMATION FOR SEQ ID NO:6:

(i) SEQUENCE CHARACTERISTICS:
        (A) LENGTH: 79 amino acids
        (B) TYPE: amino acid
        (D) TOPOLOGY: linear (ii) MOLECULE TYPE: protein (xi) SEQUENCE DESCRIPTION: SEQ ID NO:6:

```
Asp Ala Asp Lys Asn Asp Pro Ala Gly Lys Asp Gln Gln Val Asn Val
1               5                   10                  15

Gly Glu Thr Pro Lys Ala Glu Asp Ser Ile Gly Asn Leu Pro Asp Leu
            20                  25                  30

Pro Lys Gly Thr Thr Val Ala Phe Glu Thr Pro Val Asp Thr Ala Thr
            35                  40                  45

Pro Gly Asp Lys Pro Ala Lys Val Val Val Thr Tyr Pro Asp Gly Ser
        50                  55                  60

Lys Asp Thr Val Asp Val Thr Val Lys Val Val Asp Pro Arg Thr
65                  70                  75
```

PROTEIN RIB, A CELL SURFACE PROTEIN THAT CONFERS IMMUNITY TO MANY STRAINS OF THE GROUP B STREPTOCOCCUS: PROCESS FOR PURIFICATION OF THE PROTEIN, REAGENT KIT AND PHARMACEUTICAL COMPOSITION

This application is a continuation-in-part of application Ser. No. 08/487,675 filed on Jun. 7, 1995 now U.S. Pat. No. 5,869,064, which is a continuation of PCT International Application No. PCT/SE94/00246, filed on Mar. 21, 1994 which designated the United States which claims priorty to PCT/5893/002348, filed Mar. 19, 1993. The entire contents of both of these applications are hereby incorporated by reference.

This invention relates to a novel protein designated Rib (and subfragments, variants and multiples thereof) which confers immunity to most invasive strains of the group B Streptococcus, DNA sequences encoding the protein or functional fragments or domains of the protein, DNA sequences which hybridize under stringent conditions to the DNA encoding the protein, a procedure for purification of the protein, antibodies specific to the protein, a reagent kit and a pharmaceutical composition comprising the protein or fragments thereof.

During the last three decades, the group B Streptococcus has emerged as a major cause of neonatal disease in the Western world. In the United States alone, there are about 10,000 cases per year of invasive disease caused by this bacterium. These infections have an overall mortality of about 20%, and many of the infants that survive have permanent neurological sequelae. In view of these findings, a large effort has been made to find methods of prevention and treatment and to analyze the mechanisms by which group B streptococci cause infections.

About 20% of all women are vaginal carriers of the group B Streptococcus, and vertical transmission from the maternal genital tract is probably the most common source of infection in neonatal disease caused by this bacterium. However, only 1 to 2% of the infants that are colonized by the group B Streptococcus at birth are afflicted by serious infection. Other factors than exposure to the bacterium during birth must therefore contribute to the development of neonatal disease. Mothers of infected infants have significantly lower levels of antibodies to the type III capsule, which implies that these antibodies are important for protection against neonatal disease (Baker, C. J. and D. L. Kasper, N. Engl. J. Med. 1976, 294: 753).

Group B streptococcal strains are divided into four major serotypes (Ia, Ib, II, and III) based on the structure of the polysaccharide capsule (Baker, J Inf Dis 1990. 161: 917). Serotypes I, II, and III occur in roughly equal proportions among strains in the normal flora, but type III accounts for about two-thirds of all isolates from invasive infections. Since the capsule is a known virulence factor, it has been studied in considerable detail, in particular in type III strains. Efforts have been made to develop a vaccine, in which the type III polysaccharide capsule would be an essential component. However, use of the polysaccharide capsule as a vaccine may give problems due to crossreactions with human tissues (Pritchard et al., Infect Immun 1992. 60: 1598). It would therefore be very valuable if one could develop a vaccine based on proteins rather than on polysaccharides.

The group B Streptococcus can also cause mastitis in cows, a bovine disease that is of considerable economical importance. Development of a vaccine against group B streptococcal infections is therefore of interest also in veterinary medicine.

Two group B streptococcal cell surface proteins have previously been studied in detail: the alpha and beta proteins. These proteins confer protective immunity to strains expressing the proteins, but they are of limited interest for group B streptococcal disease, since they are usually not expressed by type III strains, which cause the majority of serious infections.

The present invention relates to a streptococcal cell surface protein, and variants and subfragments thereof. This protein, which is designated protein Rib, was isolated from a group B streptococcal strain of serotype III as a distinct 95 kD protein. Protein Rib is expressed by almost all group B streptococcal strains of serotype III and by a few strains of other serotypes such as II. A method has been devised to purify protein Rib and it has been demonstrated that antibodies to this protein protect against lethal infection with strains expressing protein Rib.

The invention also relates to naturally occurring and artificially modified variants, subfragments and multiples of the Rib protein which have the ability to protect against infections caused by protein Rib expressing bacteria, i.e., especially group B streptococcal strains of serotype III.

The invention also relates to a vector, such as a plasmid, a cosmid or a phage, containing the genetic code for protein Rib and variants, subfragments and fragments thereof, suitable for insertion in a non-human host organism and expression from said host. The invention particularly relates to three phage clones, lambda Rib1-3, lambda Rib1-5 and lambda Rib1-7, having deposit numbers DSM 9039, DSM 9040 and DSM 9041, respectively.

The invention also relates to a DNA sequence encoding protein Rib and variants, subfragments fragments and multiples thereof, that may be inserted in a suitable vector, such as a plasmid, a cosmid or a phage. The DNA sequence can be obtained from the deposited phages lambda Rib1-3, lambda Rib1-5 och lambda Rib1-7.

The Rib protein is expressed by different type III strains. Extracts prepared from several different strains that were analyzed by Western blotting, using anti-Rib serum for the analysis, showed that almost all extracts contained protein Rib, but the molecular mass of the protein varied between 65 and 125 kD (data not shown). This result was not unexpected, since size variation has previously been described also for other group B streptococcal proteins, the alpha and beta proteins.

The available data suggest that the protein may consist of multiples of units, each unit corresponding to a molecular mass of about 9 kD. The invention therefore includes subfragments and multiples of the 95 kD protein or of a basic unit with the same characteristics. Variants include substitution or insertions of amino acids without changing the ability to protect against infections caused by bacterias expressing the protein.

Group B streptococcal strains are well known and may be isolated from the blood of infected human beings. The BM110 strain used by the inventors was obtained from Dr. S. Mattingly (University of Texas, San Antonio, Tex.) . All strains referred to herein are obtainable from the inventors at the University of Lund and the Lund University Hospital (Doctor Gunnar Lindahl, Department of Medical Microbiology, Sölvegatan 23, S 22362 Lund, Sweden).

Protein Rib may be isolated from group B streptococcal strains of serotype III, preferably from strain BS30 or BM110. The invention concerns a process for purification of protein Rib.

The protein may be isolated by the following procedure: A Streptococcus Group B strain expressing the protein is cultivated, the medium and/or the microorganism are isolated, the bacteria are digested with an enzyme, preferably mutanolysin, a protease inhibitor is optionally added, the digested bacteria are separated from the supernatant and protein Rib is extracted from the supernatant. The media can be any media suitable for cultivation of streptococci, such as Todd-Hewitt broth (Oxoid) and the cells are preferably cultivated 1–30, especially 12–20 hours. The digestion with an enzyme, preferably mutanolysin, is performed without shaking for 1–30, especially 10–20, preferably 15–18 hours at 20–40° C., preferably 37° C. The protein may be isolated from the medium, and in such a case there is no need for digestion with the enzyme which is used to break the cell walls. A protease inhibitor such as benzamidine chloride, iodoacetic acid or phenylmethyl sulfonyl fluoride is added to prevent the action from proteases which may contaminate the mutanolysin or may be present in the microorganisms.

The protein can be purified by ion exchange chromatography, preferably anion exchange chromatography and gel filtration, and fractions containing the protein collected according to established practice within the art.

The invention especially concerns a substantially pure protein Rib or subfragments thereof. With the expression "substantially pure" we understand a substance that does not contain pharmaceutically harmful substances.

The invention also concerns antibodies corresponding to protein Rib and subfragments, variants or multiples thereof. It is well known how to immunize an animal with an antigen, in this case protein Rib, collect the blood, isolate the serum and use the antibodies that react with the protein. The serum or an IgG fraction containing the antibodies may be used in analyzing the protein.

Since antibodies to protein Rib can protect against lethal infection with group B streptococcal strains, a method to measure the level of such antibodies can be valuable, for example in order to estimate if a pregnant woman has antibodies enough to protect the baby from such an infection. Protein Rib or subfragments thereof can be used to detect such antibodies to the protein. The invention therefore also concerns a reagent kit containing protein Rib or subfragments thereof.

The present invention further includes a method of immunizing an animal such as a rodent or human with the purified Rib protein. Pharmaceutical compositions containing either Rib protein or fragments or variants thereof which confer immunity against Group B streptococcal type III proteins or antibodies which recognize Rib protein are further contemplated by the present invention. Such pharmaceutical compositions further comprise suitable pharmaceutical carriers.

It can also be of interest to analyze various samples for the presence of protein Rib. Antibodies to the protein can be used for this purpose. The invention therefore also concerns a reagent kit, comprising antibodies to protein Rib or subfragments thereof, for detection of the protein. A reagent kit may contain any of the above mentioned blood fractions containing the antibodies. It may also contain the protein, subfragments or multiples thereof for use as a standard.

The properties of protein Rib indicate that this protein can be used for the development of a vaccine against the group B Streptococcus. The invention therefore also concerns a pharmaceutical composition comprising the protein or fragments thereof as active ingredients, possibly together with pharmaceutically acceptable adjuvants and excipients. Suitable pharmaceutically acceptable adjuvants are those conventionally used in this field. Examples of suitable excipients are mannitol, lactose, starch, cellulose, glucose, etc., only to mention a few. The examples given of the adjuvant and the excipients are not to be regarded as limiting the invention.

BRIEF DESCRIPTION OF THE DRAWINGS

The invention will now be described in more detail, with the accompanying drawings, in which:

FIG. 7. Nucleotide sequence SEQ ID NO:3 of the rib gene from strain BM110 and deduced amino acid sequence. The sequence is divided into a 5' part, a central part with 12 identical repeats and a partial repeat, and a 3' part. The box indicates a possible ribosomal binding site. The vertical arrow indicates the end of the signal sequence. The dashed line indicates the $NH_2$-terminal sequence determined for protein Rib from strain BM110. The horizontal arrows indicate the position of the repeats as well as of a partial repeat. The sequence data have been submitted to the GenBank™ data base (accession no U58333).

FIGS. 9A and 9B. Comparison of the Rib SEQ ID NO:4 and α proteins. FIG. 9A shows the alignment of the amino acid sequences of Rib from strain BM110 and α from strain A909. The two vertical arrows indicate the ends of the signal sequences. The repeat regions are shown in the shaded box. Only one full repeat from each protein is shown, followed by the partial repeat. FIG. 9B shows the overall structure of Rib from strain BM110 and α from strain A909 and degree of amino acid residue identity between different regions of the proteins. S, signal peptide; N, $NH_2$-terminal region; R, one repeat; P, partial repeat; C, COOH-terminal region. The number of amino acids in each region is indicated. The Rib protein has 12 repeats of 79 amino acids and the α protein has 9 repeats of 82 amino acids.

FIG. 10A, binding of anti-Rib serum to immobilized Rib. FIG. 10B, binding of anti-α serum to immobilized α.

FIG. 11A, relationship between acrylamide concentration and apparent molecular mass in SDS-PAGE. FIGS. 11B and 11C, stained SDS-PAGE gels of purified Rib, α and β proteins analyzed at acrylamide concentrations of 5% (FIG. 11B) and 10% (FIG. 11C). The preparations of Rib and α give rise to one major band and one minor band. The molecular mass was determined for the major band. Molecular mass markers (in KDa) are shown to the right in each gel.

FIG. 12A, Western blot analysis of purified preparations of the Rib, α and β proteins under standard conditions, using specific rabbit antisera. Molecular mass markers are in kDa. FIG. 12B, proteins adjusted to pH 4.0 and then boiled with sample buffer for 5 min. Stained gel, 10% acrylamide. FIG. 12C, proteins adjusted to pH 4.0 and then boiled with sample buffer for 15 min. Stained tricine gel, 16.5% acrylamide. In gels of FIGS. 12B and 12C, molecular mass markers (in kDa) are included in the figure. FIG. 12D, overall structure of the mature Rib and α proteins. Amino-terminal sequences and putative acid-sensitive Asp-Pro (DP) sites are indicated. The bars denoted a–d show possible structures for the fragments indicated in FIGS. 12B and 12C. N, $NH_2$-terminal non-repeated region; R, one repeat.

Figure 1A:
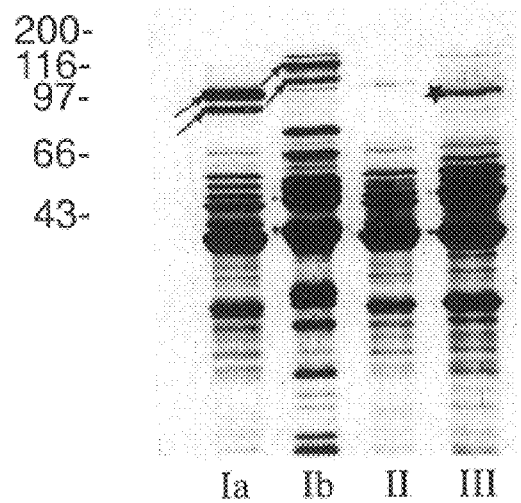
FIGS. 1 A&B.
FIG. 1B shows a Western blot analysis of extracts prepared from group B streptococcal strains representing the four main serotypes (type Ia: strain A909; type Ib: SB35; type II: B1284; type III: BS30) of FIG. 1A. As shown in the immunoblot, the strains of types Ia and Ib express the alpha and beta proteins, and the positions of these proteins in the stained gel are indicated by arrows (lower arrow: alpha antigen; upper arrow: beta antigen). The position in the stained gel of the 95-kD protein Rib of the type III strain BS30 is indicated by a star. Molecular mass markers, indicated on the left, are in kD.
Figure 1B:
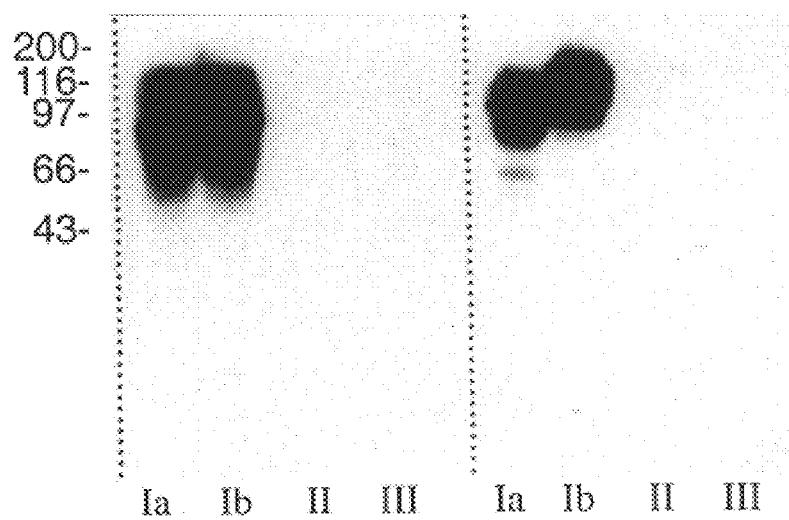
Figure 2A:
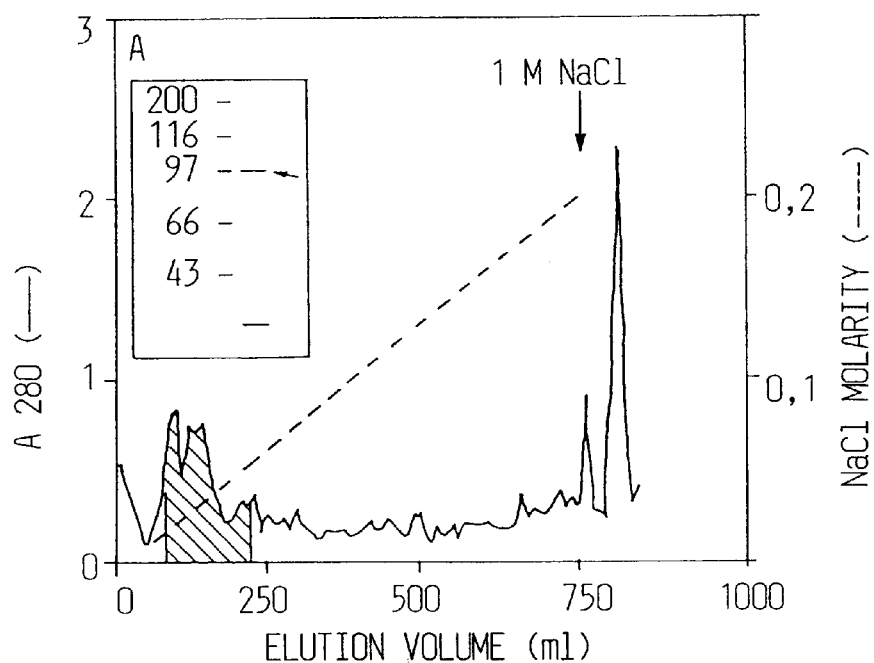
FIGS. 2A and 2B show purification of protein Rib from the type III strain BS30. (2A) A mutanolysin extract, partially purified through a previous step of DEAE ion exchange chromatography, was subjected to ion exchange chromatography on a 30 ml column of DEAE Bio-Gel A, which was eluted with a linear gradient (800 ml) of NaCl in 10 mM Tris, pH 8.0, followed by 1 M NaCl (60 ml). The shaded area indicates fractions containing protein Rib. The insert shows a pool of the protein Rib-containing fractions analyzed by SDS-PAGE; molecular mass markers, indicated on the left, are in kD, and the position of protein Rib (95 kD) is indicated by an arrow. (2B) The pool of protein Rib-containing fractions from the ion exchange chromatography was subjected to gel filtration on a column (4.2×90 cm) of Sepharose CL6B. The shaded area indicates fractions containing protein Rib and the insert shows a pool of these fractions analyzed by SDS-PAGE. $V_o$, void volume; $V_t$, total volume.
Figure 2B:
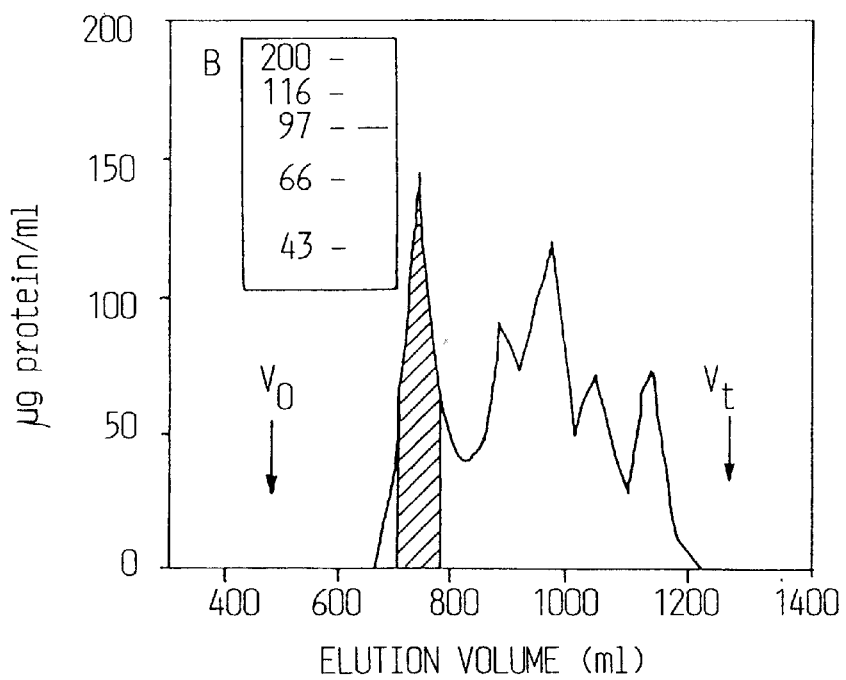

Mutanolysin extracts of several strains of different serotypes were analyzed by SDS-PAGE and by immunoblotting, using antisera to the alpha and beta proteins, see example 1. Results obtained with four strains representing the four major serotypes are shown in FIG. 1. The alpha and beta proteins, which are expressed by both the type Ia strain and the type Ib strain, gave rise to distinct bands in the high molecular weight region of the stained gel. These proteins vary in size between the two strains, in agreement with previous observations. A major protein species in the high molecular weight region was present also in the extract prepared from the type III strain, although this strain does not express the alpha protein or the beta protein. Such a distinct protein species of high molecular weight was also observed in extracts of other type III strains, and the protein appeared to vary in size between different strains. These similarities to the alpha and beta proteins made it of interest to study the high molecular weight proteins of type III strains in more detail. Strain BS30 was chosen for this work, because it was known to be mouse virulent. The 95-kD protein expressed by this strain (FIG. 1) was purified (Example 2) from mutanolysin extracts, using two consecutive steps of ion exchange chromatography, followed by gel filtration (FIG. 2). Fractions were analyzed by SDS-PAGE for presence of the 95-kD protein. When appropriate fractions from the gel filtration were pooled and analyzed, only two protein species were found: a major 95-kD protein and a minor 90-kD protein (see insert in FIG. 2B) . The 90-kD protein most likely represents a degradation product of the 95-kD protein, since these two proteins were later shown to have the same $NH_2$-terminal sequence. The purified protein is referred to as protein Rib (resistance to proteases, immunity, group B). Antiserum to the 95-kD form of protein Rib was prepared by immunizing rabbits with slices cut out from SDS-PAGE gels.

To analyze whether protein Rib is a cell surface protein, strains representing the four major serotypes were tested for ability to bind anti-Rib serum (FIG. 3). The five strains studied included the four strains described above and an additional type III strain, BM110, which is a member of the high-virulence type III clone. For comparison, these five strains were also tested for expression of the alpha and beta proteins, using antisera to highly purified preparations of these proteins.

Figure 3A:
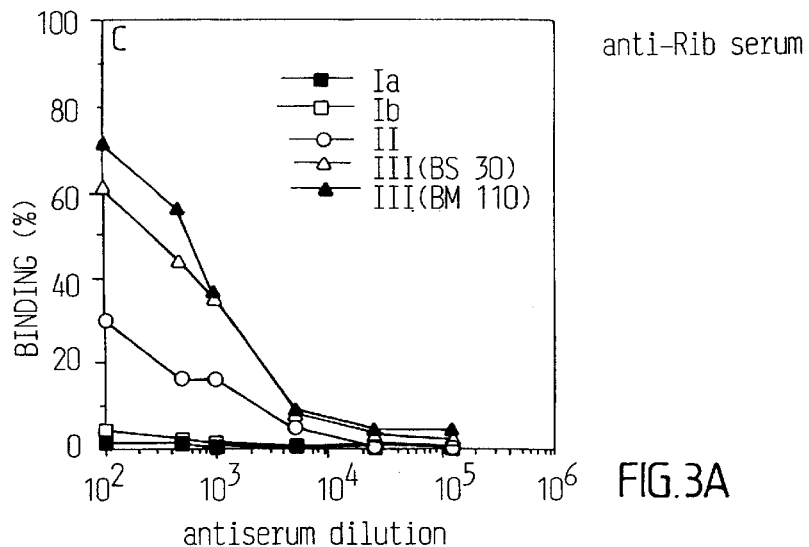
FIGS. 3A, 3B and 3C show analysis of group B streptococcal strains of the four major serotypes for cell surface expression of the alpha, beta and Rib proteins. Five strains were tested: A909 (type Ia); SB35 (type Ib); B1284 (type II); BS30 (type III), and BM110 (type III). The symbols used for these five strains are shown in panel 3C. Bacterial suspensions were incubated with different dilutions of rabbit antiserum to the alpha FIG. 3C, beta FIG. 3B, or Rib FIG. 3A protein, as indicated FIGS. 3A, B&C. The numbers on the x-axis refer to final antibody dilution in the bacterial mixture. Bound antibodies were detected by incubation with radiolabelled protein G. Controls with preimmune rabbit serum were included in all experiments and were completely negative in all cases.
Figure 3B:
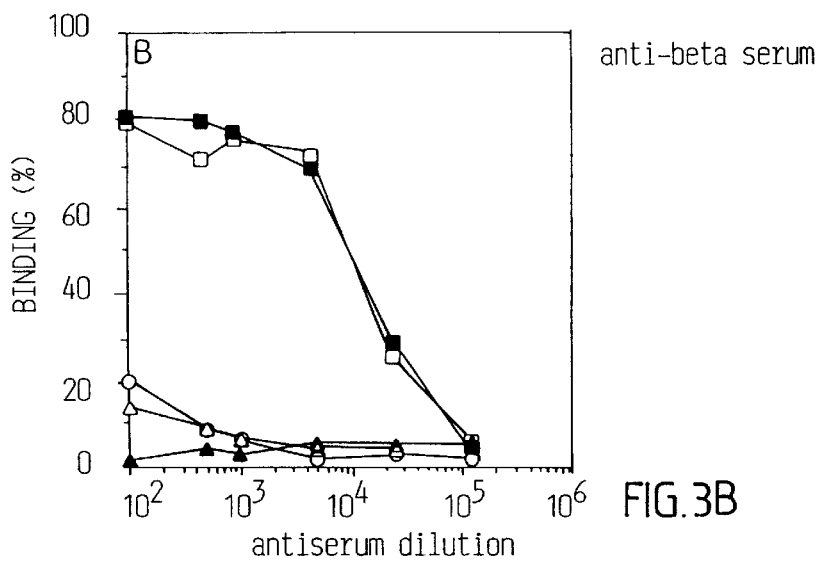

The anti-alpha serum reacted strongly with the Ia and Ib strains, as expected, and it also reacted weakly with the two strains of type III (FIG. 3A). However, mutanolysin extracts of the type III strains did not contain any detectable alpha protein, when analyzed in a Western blot. It therefore seems likely that this weak reactivity of anti-alpha serum with whole bacteria of type III represents a cross-reactivity with some other cell wall component. These data show that reactivity with anti-alpha serum can be used to unequivocally analyze whether a strain expresses the alpha antigen on the cell surface. Similar data were obtained with anti-beta serum (FIG. 3B).

Figure 3C:
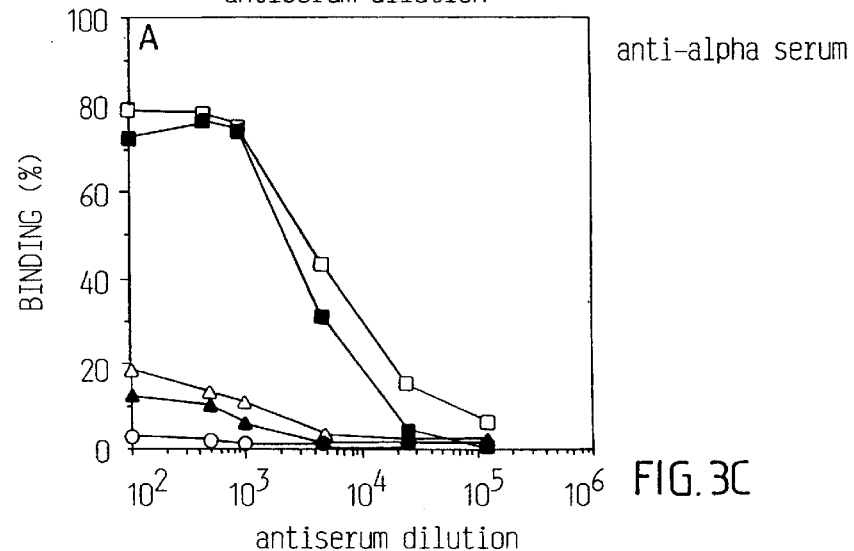

The antiserum to protein Rib reacted with the two type III strains, but not with the type Ia and Ib strains (FIG. 3C). An intermediate level of binding was observed for the type II strain. When mutanolysin extracts of the five strains were analyzed in a Western blot experiment, using anti-Rib serum for the analysis, the extracts of the type III strains reacted strongly, giving major blotting bands at 95 kD, but the extracts of the three other strains completely lacked reactivity (data not shown). This result indicates that the intermediate reactivity of anti-Rib serum with the type II strain was due to a crossreactivity, which disappeared under the conditions of the Western blot. We conclude that protein Rib is expressed on the cell surface of the two type III strains, but not on the other three strains.

A total of 58 strains of known serotype, all of which had been isolated from invasive infections, were then tested for ability to bind antibodies to protein Rib (see Table 1, example 6). Each strain was also tested for binding of antibodies to the alpha and beta proteins. To simplify the study of many strains, each antiserum was tested at a single 1000-fold dilution, chosen on the basis of the data shown in FIG. 3. This type of analysis gave unequivocal results, summarized in Table 1 of example 6. Protein Rib was found on the cell surface of 31 out of 33 type III strains and on one out of 13 type II strains, but not on any of the 12 strains of types Ia and Ib.

It seemed possible that strains lacking protein Rib on the cell surface excrete the protein into the medium. Culture supernatants of the 58 strains listed in Table 1 were therefore analyzed in a dot-blot experiment, using anti-Rib serum for the analysis. Protein Rib was not detected in the supernatants of any of the 26 strains that do not express the protein on the cell surface, but was found in the supernatants of 26 of the 32 strains expressing the protein on the cell surface (data not shown).

A mouse protection model was used to study whether rabbit antibodies to protein Rib can protect against lethal infection with the group B Streptococcus (Table 2, Example 7). Control animals received antiserum to the alpha protein or preimmune serum, as indicated. The data show that antiserum to protein Rib protects mice against lethal infection with strains expressing protein Rib.

Figure 4A:
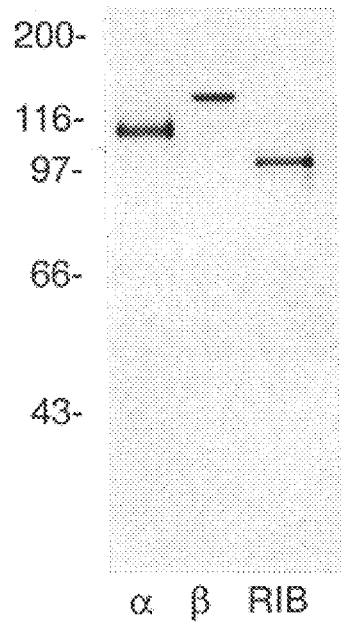
FIGS. 4A&B.
Figure 4B:
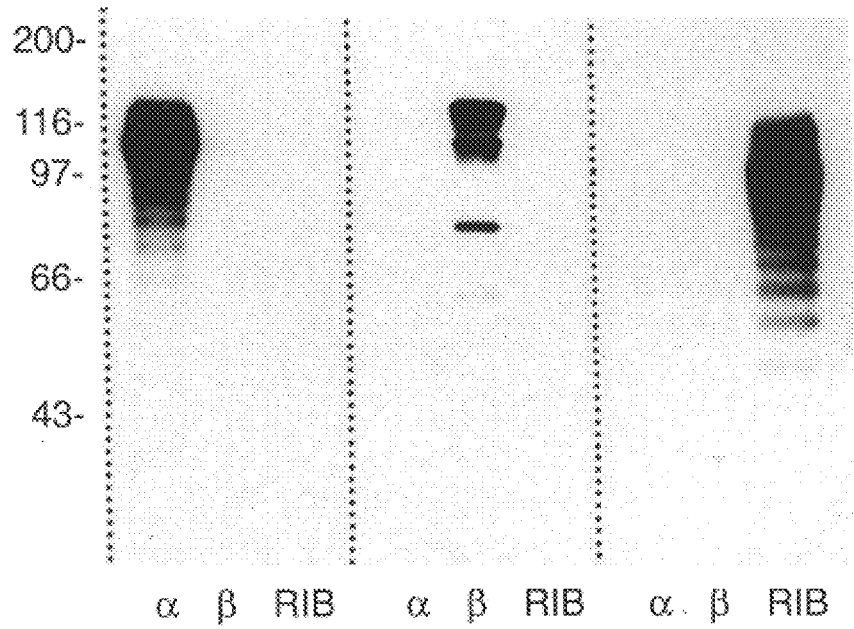
FIG. 4B shows Western blot analysis of purified alpha, beta, and Rib proteins of FIG. 4A with rabbit antisera raised against the purified proteins. Antisera were used at a 1:1,000 dilution, and bound antibodies were detected with radiolabelled protein G. Molecular mass markers, indicated on the left, are in kD.

Since protein Rib confers protective immunity, like the alpha and beta proteins, it was of interest to compare these three proteins. A Western blot experiment was performed, using antisera to the purified proteins for the analysis (FIG. 4). The staining gel showed that the three proteins were highly purified, with one major species in each preparation, but there was no serological cross-reaction between the three proteins, as shown in the Western blot.

Figure 5A:
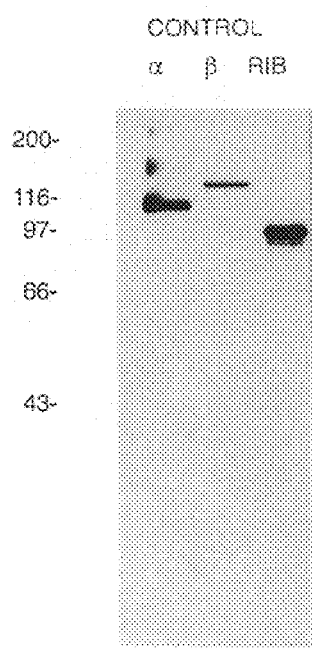
FIGS. 5A–C shows SDS-PAGE analysis of the purified alpha, beta, and Rib proteins treated with trypsin FIG. 5B or pepsin FIG. 5C. The trypsin treatment was performed at pH 7.5, the pepsin treatment at pH 4.0. The samples were neutralized before the SDS-PAGE analysis. Controls FIG. 5A were treated in the same way as the samples containing trypsin or pepsin, but no enzyme was added; such treatment did not cause degradation of the proteins. P=pepsin; T=trypsin. Molecular mass markers, indicated on the left, are in kD.
Figure 5B:
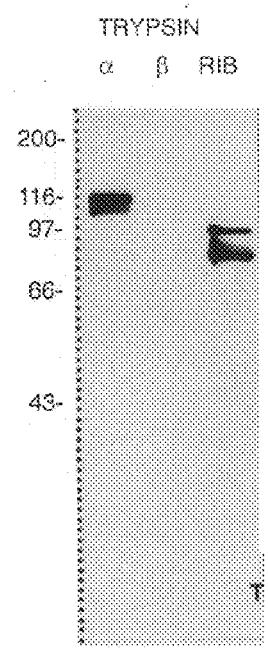
Figure 5C:
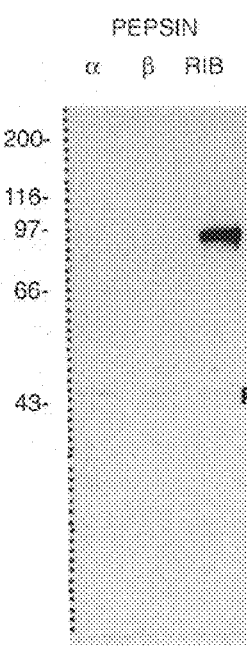

The alpha and beta proteins were originally distinguished due to a difference in protease sensitivity. The alpha protein is resistant to trypsin but sensitive to pepsin, while the beta protein is sensitive to both of these proteases (Bevanger and Maeland, *Acta Path Microbiol Scand Sect B* 1979. 87: 51). An experiment with the purified alpha and beta proteins confirmed this difference and also demonstrated that protein Rib is resistant to both trypsin and pepsin (FIG. 5). As expected, all three proteins were sensitive to degradation by proteinase K (data not shown). The protease resistance of protein Rib was not due to the presence of an inhibitor, since beta protein was completely degraded by both trypsin and pepsin even in the presence of protein Rib (data not shown).

The sequence of the entire rib gene and the deduced amino acid sequence of the Rib protein are shown in FIG. 7 (SEQ ID NO: 3). Comparison of this sequence with the $NH_2$-terminal sequence of Rib demonstrated that the signal sequence has a length of 55 amino acid residues. A region with 12 identical repeats (each with a length of 79 amino acid residues) (SEQ ID NO: 5) and a partial repeat (15 amino acid residues) accounts for >80% of the sequence of the mature protein. As described below, the repeats are apparently identical even at the DNA level. The processed form of protein Rib has a length of 1176 amino acid residues and a predicted molecular mass of 123 kDa.

Initially, a λEMBL3 clone expressing protein Rib was isolated and used to construct the subclone pGRib105 (Example 9). Preliminary sequence analysis of pGRib105 allowed the identification of the 5' and 3' ends of the rib gene. Analysis of the central part of the gene showed that partial digestion with BglII gave rise to a regular ladder pattern on agarose gels, indicating the existence of repeated sequences containing BglII sites. Sequence analysis indeed demonstrated the presence of repeats corresponding to 79 amino acid residues. This initial analysis indicated that Rib has a highly repetitive structure.

Figure 8:
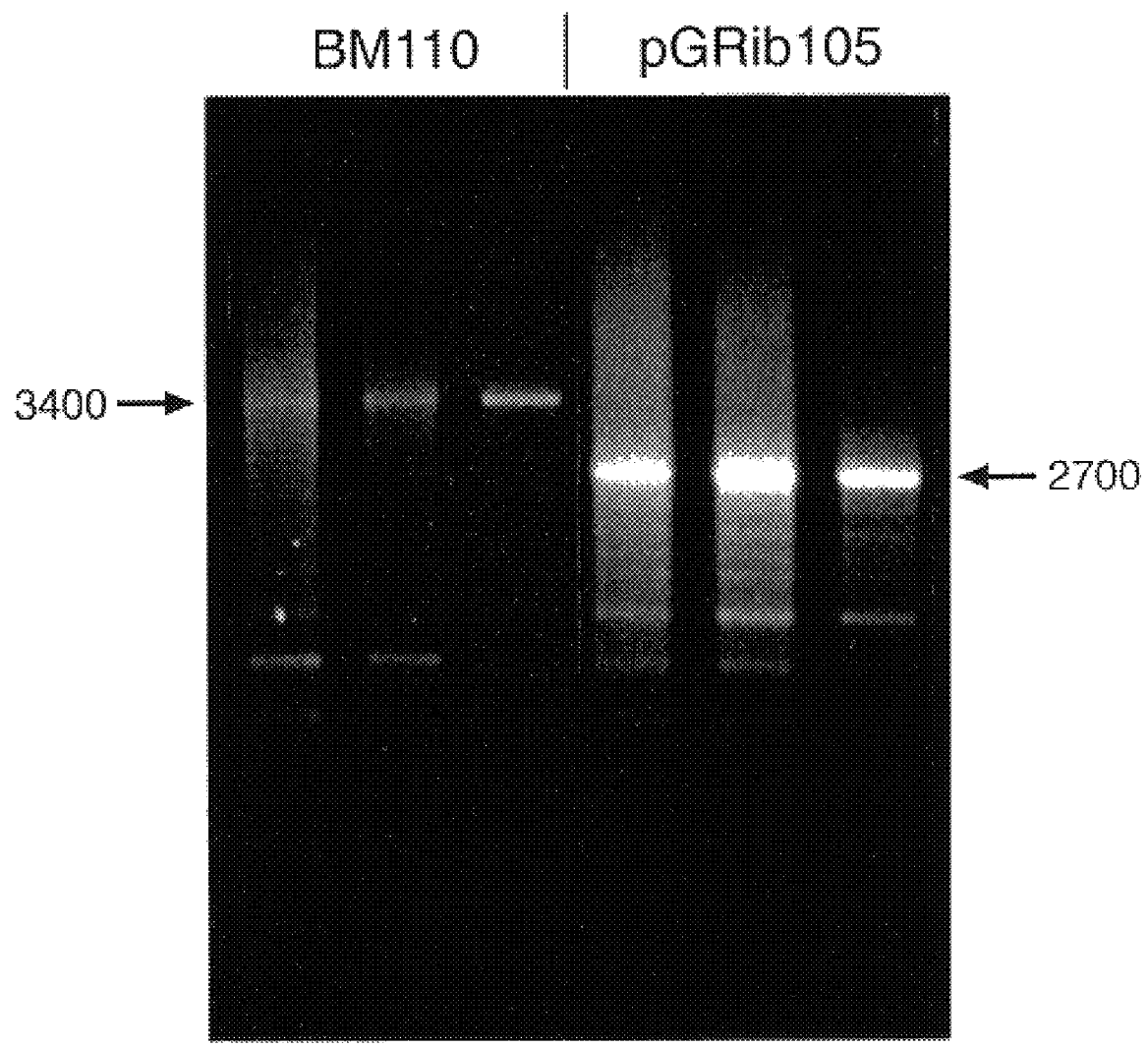
FIG. 8. PCR analysis of the rib gene. PCR products were generated, from streptococcal strain BM110 DNA and from the plasmid clone pGRib105, using fivefold dilutions of the templates. Sizes (in bp) of the main PCR products are indicated. The PCR product of 3,400 bp corresponds to a rib gene with 12 complete repeats and the PCR product of 2,700 bp corresponds to a rib gene with 9 complete repeats.

To further characterize the repeat region, PCR analysis was performed, allowing amplification of the whole rib gene (Example 9). For chromosomal DNA, the main PCR product had a size of ~3,400 bp, corresponding to a rib gene with 12 repeats. However, the pGRib105 subclone generated a main PCR band of ~2,700 bp, corresponding to a rib gene with 9 repeats, implying that part of the repeat region had been lost during the initial cloning in the λ vector. An interesting observation made during the PCR analysis was that the PCR product not only contained the main band but also gave rise to a ladder of bands with a size difference of ~237 bp, corresponding to one repeat (FIG. 8). This ladder could be the result of slippage of Taq polymerase during replication, due to the unique repetitive structure of the rib gene.

Based on the results of the PCR analysis, attempts were made to clone the entire rib gene in *E. coli*. Since it seemed possible that Rib had a toxic effect on *E. coli*, the rib gene was cloned without the promoter and signal sequence regions. Appropriate fragments of chromosomal DNA from strain BM110 were cloned directly into the pGEM7Z(f+) vector, generating clone pGRib116. Initial analysis of this clone showed that it contained a repeat region of the same size as the chromosomal rib gene. However, further analysis of pGRib116 indicated that the repeat region in this clone was highly unstable, although it was maintained under Rec⁻ conditions and not expressed. Since the entire repeat region of the rib gene could not be stably maintained in *E. coli*, it was not possible to analyze the sequence of this region with standard methods.

To analyze the sequence of the repeat region, individual repeats cloned at random were sequenced. As described above, the analysis of the rib gene had indicated that all repeats contained a unique BglII site. Therefore cloned fragments were obtained by BglII digestion of plasmid pGRib116, assuming that they would be representative of the whole repeat region. A total of 13 repeats were analyzed and all of them were found to have identical nucleotide sequences. The conclusion that all repeats are identical was further supported by analysis of sequences at the extremities of the repeat region. The 5' half of the first repeat (up to the BglII site) and the 3' half of the last complete repeat (downstream from the BglII site) together formed a repeat whose nucleotide sequence was identical to that of repeats recovered after BglII digestion. In addition, the partial repeat (coding for 15 amino acid residues) had a nucleotide sequence identical to the corresponding region in the complete repeats.

Comparison Between the Rib and α Proteins

Previous studies have shown that the α protein of GBS has a very repetitive structure, with long repeats that are identical even at the DNA level (Michel, J. L., Madoff, L. C., Olson, K., Kling, D. E., Kasper, D. L. and Ausubel, F. M.

(1992) Proc. Natl. Acad. Sci. U.S.A. 89 10060–10064). As shown in FIG. 9, α protein and Rib protein of GBS exhibit extensive amino acid residue identity. The signal sequences show 80% residue identity and are unusually long: 55 residues in protein Rib (FIG. 7) and 56 residues in the α protein (Stalhammar-Carlemalm, M., Stenberg, L. and Lindahl, G. (1993) J. Exp. Med. 177 1593–1603). In the non-repeated $NH_2$-terminal parts of the mature proteins (174 and 170 residues, respectively) the degree of residue identity is 61%. The repeats (79 and 82 residues, respectively) show a somewhat lower degree of residue identity, 47%. The short COOH-terminal regions of the two proteins are almost identical and have the characteristics of cell wall attachment regions in surface proteins of Gram-positive bacteria, including an LPXTG sequence (Schneewind, O., Mihaylova-Petkov, D. and Model, P. (1993) EMBO J. 12 4803–4811).

The Rib and α proteins have an unusually high content of Asp, Val, Thr, Pro, and Lys, which together account for about 60% of the amino acid residues in each protein. Computer assisted analysis indicated that the Rib and α proteins are highly acidic, with isoelectric points of 4.3 and 4.5, respectively. Analysis of the protein sequences by protein structure algorithms (Genetics Computer Group (1994) Program Manual for the GCG Package, Version 8, University of Wisconsin, Madison Wis.; and the GeneWorks program), predicted a high β-sheet content in each protein, including the repeat regions.

Immunological Relationship Between the Rib and α Proteins

Figures 10A, 10B:
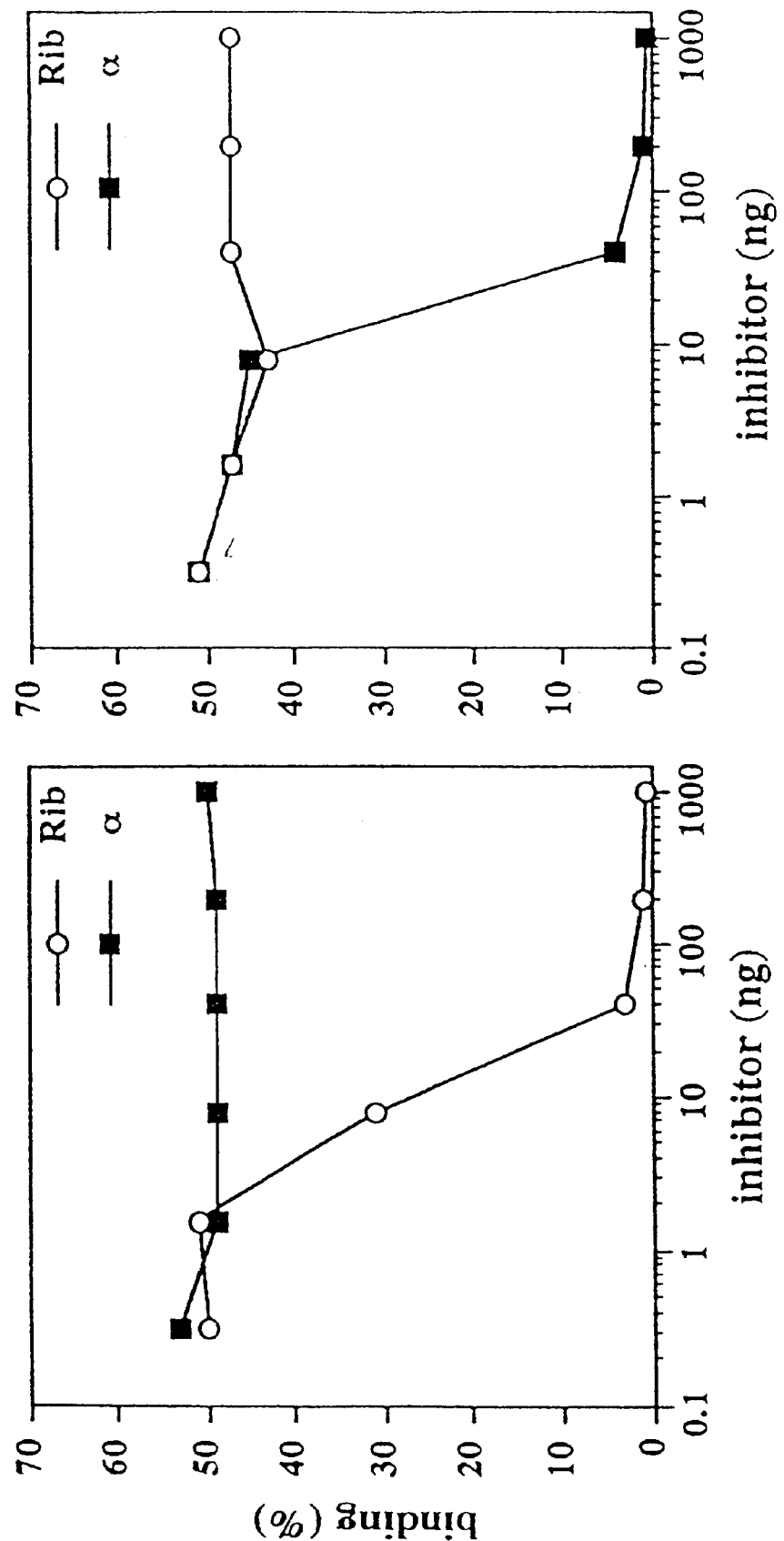
FIGS. 10A and 10B. Immunological relationship between the Rib and α proteins, analyzed by solid phase radioimmunoassay. Highly purified preparations of Rib or α were immobilized in microtiter wells and allowed to react with rabbit antibodies to the corresponding protein. The reactions were inhibited by the addition of increasing amounts of Rib or α.

As indicated above, Rib and α proteins are immunologically unrelated, when analyzed with specific rabbit antisera in Western blots and dot-blots. However, the extensive sequence homology between the two proteins suggested that a crossreactivity might be detected if more sensitive methods were used. To analyze this possibility, inhibition tests were performed (FIG. 10). The reactivity between Rib, immobilized in microtiter plates, and anti-Rib serum was inhibited by pure protein Rib, but addition of the α protein did not cause any inhibition even when a large excess was added (FIG. 10A). Similarly, the reaction between α and anti-α serum was inhibited by purified α protein, but not by protein Rib (FIG. 10B). These results indicate that the large majority of antibodies directed against Rib or α completely lack reactivity for the heterologous antigen.

Aberrant Migration Behaviour of the Rib and α Proteins in SDS-PAGE

Figure 11A:
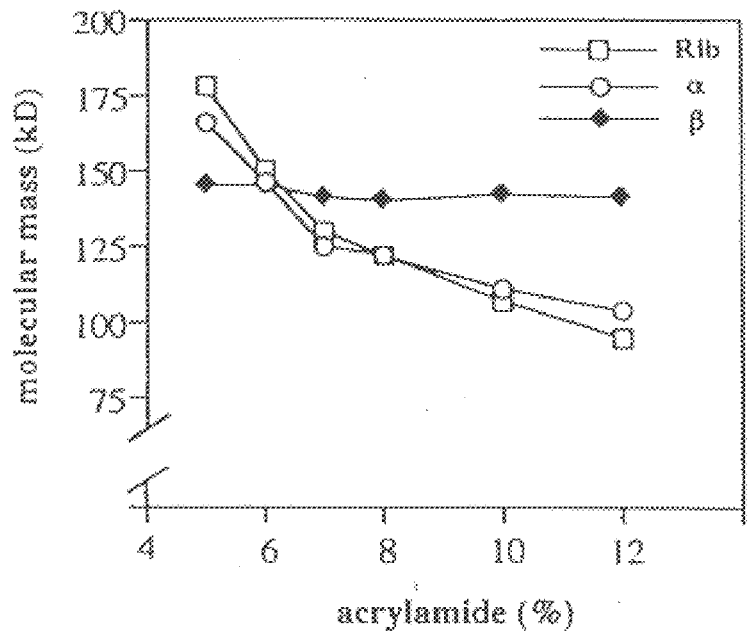
FIGS. 11A–11C. Analysis of the apparent molecular mass of the purified Rib, α, and β proteins.
Figure 11B:
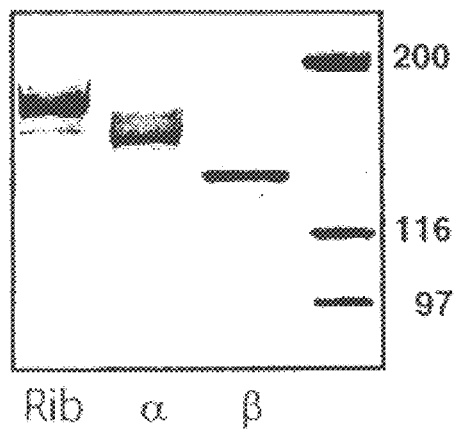
Figure 11C:
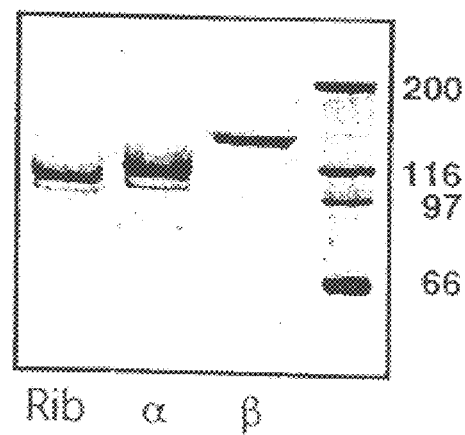

An unusual feature of Rib and α is their behaviour in SDS-PAGE gels, where the apparent molecular mass of each protein was found to vary depending on the acrylamide concentration of the gel (FIG. 11A). At an acrylamide concentration of 5% the major polypeptide species in the Rib and α protein preparations migrated at positions corresponding to molecular masses of about 178 and 166 kDa, respectively (FIG. 11B), but at an acrylamide concentration of 10% the apparent molecular masses were approximately 107 and 111 kDa, respectively (FIG. 11C). According to the deduced amino acid sequences the predicted molecular masses of the mature Rib and α proteins are 123 and 103 kDa, respectively. Unlike Rib and α, the group B streptococcal β protein, an IgA-binding surface protein that is structurally unrelated to the Rib and α proteins and lacks long repeats (Hedén, L. O. Frithz, E. and Lindahl, G. (1991) Eur. J. Immunol. 21 1481–1490 and Jerlström, P. G. Chhatwal, G. S. and Timmis, K. N. (1991) Mol. Microbiol. 5 843–849), had the same apparent molecular mass in the different SDS-PAGE gels (FIG. 11).

Analysis of Ladder Patterns Generated by the Rib and α Proteins in SDS-PAGE: Evidence for Hydrolysis of Acid-Labile Asp-Pro Bonds It has previously been reported that bacterial extracts containing the α protein give rise to a regular ladder pattern in immunoblotting experiments, indicating that the α protein is size heterogeneous (Madoff, L. C., Hori, S. Michel, J. L., Baker, C. J. and Kasper, D. L. (1991) Infec. Immun. 59 2638–2644). Interestingly, the distance between the ladder steps was found to correspond to one repeat, suggesting that the different molecular species in the ladder represented polypeptides with different number of repeats (Michel et al. (1992)). A similar ladder pattern was also observed in Western blots of the Rib protein. It may be that this size heterogeneity could be the result of early termination of translation, RNA-mediated self cleavage, acid hydrolysis, or protease activity (Michel et al. (1992)). A repetitive protein from the salivary glands of Chironomus tentans has also been shown to form a regular ladder pattern in Western blots, and it was suggested that the heterogeneity reflects a degradation that occurs naturally in the salivary glands (Galli, J. and Weislander, L. (1993) J. Biol. Chem. 268 11888–11893). It was therefore of interest to analyze the mechanism that generates such ladder patterns.

Figure 12A:
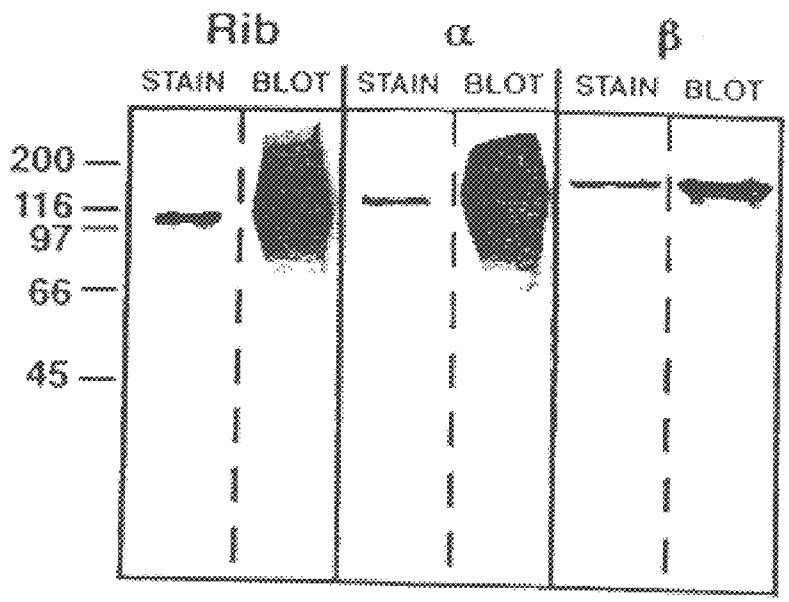
FIGS. 12A–12D. Analysis of ladder patterns formed by the Rib and α proteins in SDS-PAGE.
Figure 12B:
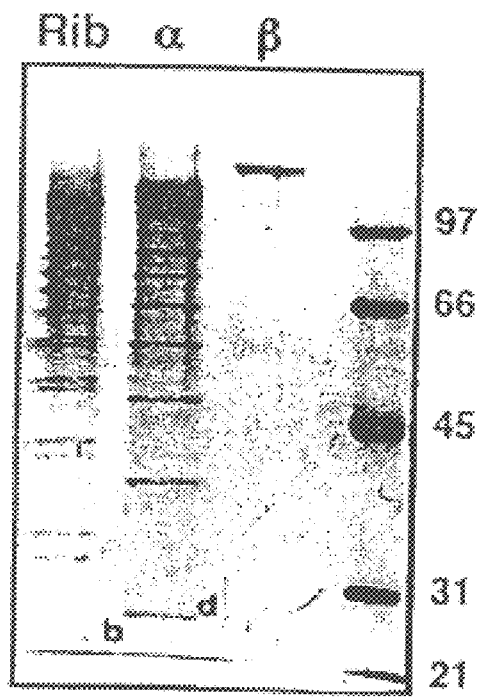
Figure 12C:
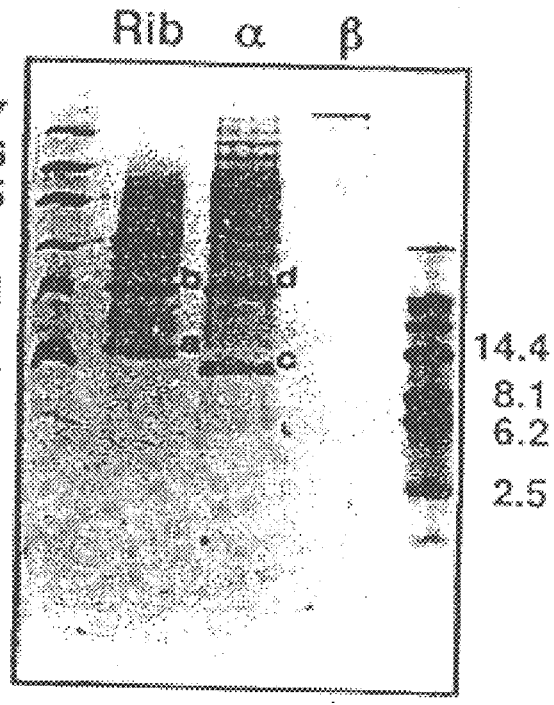
Figure 12D:
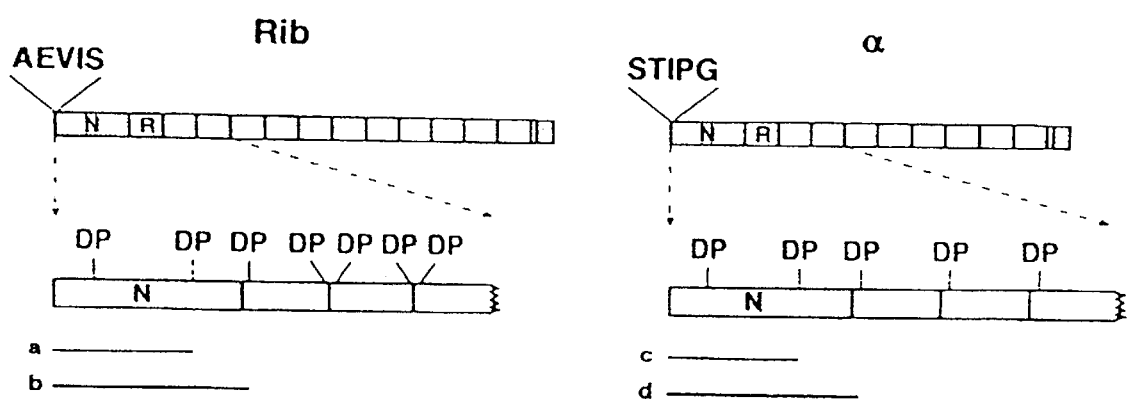

Analysis of the sequences of the Rib and α proteins suggested that the ladder pattern might be due to hydrolysis of Asp-Pro bonds, which are found in the repeats of both proteins (FIG. 12D). It is known that such bonds are sensitive to acid hydrolysis (Landon, M. (1977) Methods Enzymol. 47 145–149). To analyze whether acid-labile sites are responsible for the ladder pattern, purified preparations of the Rib and α proteins were first analyzed under standard conditions (FIG. 12A). Under these conditions, the ladder pattern was seen in blots but not in stained gels, indicating that only a small fraction of the purified proteins were of lower molecular weight and gave rise to the ladder (FIG. 12A). Next, the purified Rib and α proteins were incubated at pH 4.0 at 37° C. for 16 h before analysis. The resulting preparations were either boiled directly in sample buffer or neutralized before boiling in sample buffer. When these preparations were analyzed by SDS-PAGE, the analysis showed that distinct ladder patterns, readily detectable also in stained gels, were formed when the proteins has been boiled for 5 min in sample buffer at acidic pH (FIG. 12B). However, only a minor degradation was detected in the samples that had been neutralized before the analysis (data not shown). Thus, the ladder patterns were largely due to fragmentation during boiling in non-neutralized sample buffer (FIG. 12B). The Rib and α proteins were further degraded when the samples were boiled at acidic pH for a longer period (15 min), as detected in a stained tricine gel (FIG. 12C). In contrast, the group B streptococcal β protein, which does not contain Asp-Pro sequences, was not degraded at acidic pH (FIGS. 12B and 12C). The repeats in the Rib protein contain two Asp-Pro sites (FIG. 12D) which may explain why this protein gives rise to doublet bands (FIG. 12B).

To further analyze the formation of the ladder, bands generated by the Rib and α proteins at acidic pH were subjected to $NH_2$-terminal sequence analysis. Bands analyzed included those labeled a–d in FIGS. 12B and 12C, as well as polypeptides of higher molecular weight. All bands analyzed had sequences identical to the $NH_2$-terminal sequences of the mature proteins, i.e., AEVIS for the Rib protein and STIPG for the α protein (FIG. 12D). These data may be explained by assuming that acid hydrolysis occurred at all Asp-Pro sites in the Rib and α proteins, except the most NH$_2$-terminally located site in each protein, which would have given rise to a short NH$_2$-terminal fragment that was not detected.

Although the data reported above suggest that the ladder pattern observed for the Rib and α proteins is generated by cleavage of Asp-Pro bonds, cleavage of such bonds would be expected to generate both NH$_2$-terminal and COOH-terminal fragments as well as internal peptides generated by hydrolysis of Asp-Pro sites in the repeats (7.2 and 1 kDa peptides from the repeats of protein Rib and an 8.7 kDa peptide from the repeats of the α protein). Surprisingly, neither COOH-terminal fragments nor internal peptides were found, indicating that these peptides had been further degraded or lost during the analysis (FIG. 12C). Interestingly, the ladder pattern formed by the salivary gland protein from C. tentans also showed the absence of internal peptides corresponding to single repeats (Galli, J. (1993)).

The invention will now be described with the following examples, which however do not lEXit the scope of the invention.

EXAMPLE 1

Identification of the Protein

Four group B streptococcal strains representing the four main serotypes were used as reference strains: A909, type Ia/c; SB35, type Ib; B1284, type II; BS30, type III, described here. The BS30 strain was isolated at Lund University Hospital from a boy with neonatal infection. All bacterial strains were grown in Todd-Hewitt broth (Oxoid) at 37° C., without shaking. Mutanolysin extracts of the strains were analyzed by SDS-PAGE and by immunoblotting using antisera to the alpha and beta proteins. Small-scale mutanolysin extracts of streptococcal strains were prepared as described for the large-scale extracts used for protein purification, but cultures of only 50 ml were used to prepare 20% bacterial suspensions, of which 1 ml samples were digested with the enzyme.

SDS-PAGE was performed with standard techniques, using a total polyacrylamide concentration of 10% and a cross-linking of 3.3%. Samples were boiled for 3 min in a solution containing 2% SDS and 5% 2-mercaptoethanol prior to electrophoresis. The separated proteins were stained with Coomassie Brilliant Blue R-250 or transferred by electroblotting to a membrane of methanol-activated polyvinylidene difluoride (Immobilon-P; Millipore Corp., Molsheim, France), using a Semi-Dry Electroblotter (Ancos, Vig, Denmark). The Immobilon membranes were blocked with gelatin, using standard procedures, and then incubated with the indicated type of rabbit antiserum diluted 1000-fold (see example 7), followed by radiolabelled protein G and autoradiography.

Proteins were radiolabelled with carrier-free $^{125}$I (Amersham International, England), using the chloramine T method. Total protein concentrations were determined with the MicroBCA protein assay reagent (Pierce). Electroelution of protein from SDS-PAGE gels was performed with a model 422 Electro-Eluter from Bio-Rad.

The results are shown in FIG. 1.

EXAMPLE 2

Purification of Protein Rib

The bacteria in a 10 l overnight culture of strain BS30 were spun down, washed twice with 50 mM Tris, pH 7.3, and resuspended to 20% (v/v) in the same buffer. Mutanolysin (Sigma Chemical Co., St. Louis, Mo.), dissolved to 5000 units/ml in 10 mM potassium phosphate, pH 6.2, was then added to the bacterial suspension (125 ml) to give a final concentration of 350 units/ml. The digestion was allowed to proceed for 17 h at 37° C. with gentle shaking, and protease inhibitors were then added to the following final concentrations: benzamidine chloride, 5 mM; iodoacetic acid, 5 mM; phenylmethyl sulfonyl fluoride, 2 mM. The suspension was centrifuged and the supernatant was immediately dialyzed (dialysis tubing Spectrapor No. 4) against 10 mM Tris, pH 8.0. This dialyzed preparation was subjected to two consecutive steps of ion exchange chromatography, which allowed the best recovery of pure protein Rib, as shown by preliminary experiments. The presence of protein Rib was analyzed by SDS-PAGE and visual inspection of the gels for the presence of the 95-kD band. In the first chromatography step, the dialyzed preparation (110 ml) was mixed with the same volume of 0.4 M NaCl in 10 mM Tris, pH 8.0 and 30 ml of DEAE Bio-Gel A (BioRad Laboratories, Richmond, Calif.), equilibrated with 10 mM Tris, pH 8.0. This mixture was stirred gently at 4° C. for 1 h, and unabsorbed material (containing protein Rib) was freed from the gel by filtration through a glass filter. For the second chromatography step (FIG. 2A), the filtrate containing protein Rib was diluted twenty-fold with distilled water, to reduce the ionic strength, and mixed with 30 ml of DEAE Bio-Gel A, equilibrated as described above. After gentle stirring at 4° C. for 16 h, the gel was recovered by filtration and washed with 10 mM Tris, pH 8.0. Absorbed proteins (including protein Rib) were eluted with an 800 ml linear salt gradient (0–0.2 M NaCl in 10 mM Tris, pH 8.0), followed by 1 M NaCl (60 ml). Fractions (10 ml) were collected and those containing protein Rib were pooled, concentrated, and subjected to gel filtration in a column of Sepharose CL6B (4.2 cm×90 cm) in PBSA (0.12 M NaCl, 0.03 M phosphate, 0.02% NaN$_3$, pH 7.2) (FIG. 2B). The fractions were analyzed by SDS-PAGE electrophoresis for presence of the 95-kD band. Fractions (10 ml) containing protein Rib were pooled and frozen. The yield of protein Rib was about 6 mg from 25 g of bacteria. To ensure the purity of the protein Rib preparations used for immunochemical analysis, the protein used for such work was further purified by SDS-PAGE, followed by electroelution of the 95-kD band. However, SDS-PAGE analysis did not demonstrate any difference in purity between this electro-eluted material and that recovered from the gel filtration step.

As mentioned above, protein Rib is also found in the medium of strains expressing the protein. The protein can be purified from such a medium, using techniques similar to those described above.

Automated amino acid sequence analysis of protein bands transferred to Immobilon was performed directly on the membranes, using an Applied Biosystems 470A gas-liquid solid-phase sequenator. The membranes were lightly stained with Coomassie Brilliant Blue to localize the protein bands, which were then cut out for sequencing. The SwissProt Data Bank was used for analysis of protein sequences.

The NH$_2$-terminal sequence of protein Rib from strain BS30 is shown in SEQ ID NO:1. The two proteins with estimated molecular masses of 95 kD and 90 kD in purified protein Rib (FIG. 2B) were found to have the same NH$_2$-terminal sequence, suggesting that the smaller molecule is a degradation product of the larger one. A data search showed that the NH$_2$-terminal sequence of protein Rib is unique.

The same purification procedure was also followed for the isolation of protein Rib from strain BM110. The NH$_2$-terminal sequence (SEQ ID NO:2) of protein Rib isolated from strain BM110 may differ from the NH$_2$-terminal sequence of the corresponding protein from BS30 at position 7, where the BM110 protein may have Ser in place of Asp.

EXAMPLE 3

Purification of the Alpha Protein

The alpha protein was purified from strain SB35, a type Ib strain expressing both the alpha and beta proteins. The procedure used was similar to that used for purification of protein Rib from strain BS30. Fractions were analyzed for the presence of alpha protein by dot-blot analysis, using rabbit anti-alpha serum (kindly provided by Dr. L. Bevanger, University of Trondheim, Norway) and protein G (Calbiochem Co., San Diego, Calif.) radiolabelled with $^{125}$I. In the ion exchange and gel filtration steps, the behaviour of the alpha protein was similar to that of protein Rib (cf. FIG. 2). The alpha protein recovered from the gel filtration step was present in a sharp peak. Analysis of this material with different antisera indicated that it contained trace amounts of contaminating beta protein, which was removed by passage of the preparation through a small column of IgA-Sepharose. The purified alpha protein had a molecular weight of about 110,000, according to SDS-PAGE analysis (cf. FIG. 4). The yield of alpha protein was 12 mg from 39 g of bacteria. The alpha protein used for immunochemical work was further purified by electroelution from SDS-PAGE gels, as described above for protein Rib. However, SDS-PAGE analysis did not demonstrate any difference in purity between this electro-eluted material and that recovered from the gel filtration step.

EXAMPLE 4

Purification of the Beta Protein

The IgA-binding beta protein (Russell-Jones et al, *J Exp Med* 1984. 160: 1467) was purified by a procedure similar to that used for the Rib and alpha proteins. The starting material was obtained by incubating washed SB35 bacteria in 50 mM glycine-NaOH buffer, pH 11.0 (final pH in suspension 9.7). Previous work in our laboratory had shown that the major protein species in such an extract is the beta protein. The extract (222 ml) was immediately dialyzed against 10 mM Tris, pH 8.0, diluted twenty-fold with distilled water and mixed with 40 ml of DEAE Bio-Gel A (equilibrated with 10 mM Tris, pH 8.0). After gentle stirring at 4° C. for 2 h, the gel was transferred to a column and eluted with an 800 ml linear salt gradient (0–0.2 M NaCl in 10 mM Tris, pH 8.0). A dot blot procedure was used to test fractions (10 ml) for presence of beta protein, using radiolabelled IgA or anti-beta serum and radiolabelled protein G for the analysis. The beta protein was eluted in the first part of the gradient. Appropriate fractions were pooled, concentrated, and subjected to gel filtration on a column (4.2×100 cm) of AcA34 (Pharmacia-LKB, Uppsala, Sweden) in PBSA. The beta protein was eluted in a well-defined peak. Appropriate fractions were pooled, concentrated and frozen. The yield was 9 mg of pure protein from 23 g of bacteria. The major protein species in such a preparation had a molecular weight of about 130,000, according to SDS-PAGE, but small amounts of degradation products of lower molecular weight were also seen when the protein was subjected to Western blot analysis.

EXAMPLE 5

Analysis of Protease Sensitivity

For analysis of protease sensitivity (FIG. 5), 200 µl samples of purified alpha, beta or Rib protein (0.5 mg/ml) were incubated for 1 h at 37° C. with trypsin, pepsin, or proteinase K (0.2 mg/ml). Trypsin digestion was performed in 0.25 M sodium phosphate, pH 7.5, pepsin digestion in 0.25 M sodium acetate, pH 4.0, and proteinase K digestion in 0.25 M Tris, pH 7.4. The samples were neutralized before analysis by SDS-PAGE.

EXAMPLE 6

Analysis of Streptococcal Stains for Cell Surface Expression of the Alpha, Beta and Rib Proteins Five reference strains available in our laboratory were first analyzed for surface expression of the alpha, beta and Rib proteins. Later, a collection of 58 group B streptococcal strains, all isolated from cases of invasive infections, were also used to study the expression of these cell surface proteins (see Table 1). Typing of group B streptococcal strains was performed in the Clinical Microbiology Laboratory of Lund University Hospital, using standard techniques.

The bacteria in a 10 ml overnight culture were washed twice with PBSAT (PBSA supplemented with 0.05% Tween 20) and a 1% suspension in PBSAT was prepared. A sample (180 µl) of this bacterial suspension was mixed with 20 µl of rabbit antiserum that had been diluted in PBSAT and the mixture was incubated at 23° C. for 1 h. Two ml of PBSAT were then added, the bacteria were spun down, washed once with 2 ml of PBSAT, and resuspended in 200 µl of PBSAT. For detection of bound IgG, 25 µl of radiolabelled protein G (about $10^4$ cpm in PBSAT) was then added and incubation was continued at 23° C. for 1 h. Following addition of 2 ml of PBSAT, the bacteria were spun down and the pellet was then washed by addition of 2 ml of PBSAT. After a final centrifugation, the supernatant was discharged and the radioactivity in the pellet was determined. When many strains were tested for expression of the alpha, beta and Rib proteins (Table 1), a single final antiserum dilution of 1:1,000 was used. Controls with preimmune rabbit antiserum were always included and were completely negative in all cases. Protein Rib was found on the cell surface of 31 out of 33 type III strains, but not on any of the 12 strains of types Ia and Ib.

TABLE 1

Cell surface expression of the alpha, beta and Rib proteins by 58 group B *streptococcal* strains isolated from patients with invasive infections*

| Protein expressed | Capsular type | | | |
| --- | --- | --- | --- | --- |
| | Ia (n = 9) | Ib (n = 3) | II (n = 13) | III (n = 33) |
| alpha | 6 | 0 | 4 | 0 |
| beta | 1 | 0 | 0 | 0 |
| alpha and beta | 1 | 3 | 5 | 0 |
| Rib | 0 | 0 | 1 | 31 |
| none | 1 | 0 | 3 | 2 |

The cell surface expression of the alpha, beta, and Rib proteins was analyzed with specific antisera, and bound antibodies were detected with radiolabelled protein G, as shown in FIG. 3.

* The 58 strains studied here were all isolated from cases of invasive infections, but do not represent a random collection of such strains, since most of the type II strains were later added to the collection originally studied, which included only two type II strains.

EXAMPLE 7

Preparation of Antisera and Mouse Protection Tests

All antisera were produced in rabbits, which were immunized s.c. on the back. For preparation of antiserum to protein Rib expressed by strain BS30, slices corresponding to several 95 kD bands in SDS-PAGE gels were cut out, divided into small pieces and mixed with complete Freund's adjuvant. For the initial immunization, six slices (about 60 μg of protein) in 1 ml of PBS were mixed with 1 ml of adjuvant. Three bands (30 μg of protein) were used for booster injections. The first booster was given after 4 weeks and 3 additional boosters were given with intervals of 2 weeks. The rabbit was then bled 3 times with intervals of 3 weeks; the serum obtained from these 3 bleedings was pooled and used for the experiments reported here. Antiserum to the alpha protein was prepared by the same procedure. The first sample of anti-alpha serum, used to analyze fractions during the purification, was obtained from Dr Lars Bevanger, Trondheim. Antiserum to the purified beta protein was available in our laboratory.

C3H/HeN mice, bred in our department, were used at an age of 10–20 weeks. The mice were injected i.p. with 0.5 ml of a rabbit serum diluted five-fold in PBS, and infected 4 h later by i.p. injection of 0.5 ml of log-phase bacteria diluted in Todd-Hewitt broth. The number of bacteria used, which was estimated to be the 90% lethal dose ($LD_{90}$), was $2 \times 10^6$ c.f.u. for strains BM110, BE210, and SB35sed1, and $2 \times 10^7$ c.f.u. for BS30 and L25. Dead animals were counted daily for 4 days. Control animals usually died within 24 h.

TABLE 2

Rabbit antiserum to protein Rib protects mice against lethal infection with group B *streptococcal* strains expressing this protein

| Strain | Capsular type | Relevant cell surface protein* | Mice surviving[†] after pretreatment with | | |
|---|---|---|---|---|---|
| | | | anti-Rib serum | anti-alpha serum | normal serum |
| BS30 | III | Rib | 29/32[§] | 1/15 | 4/20 |
| BM110 | III | Rib | 15/24[§] | 0/15 | 0/15 |
| L25 | III | — | 0/15 | 2/14 | n.d.[ii] |
| BE210 | II | Rib | 10/15[¶] | 0/14 | n.d. |
| SB35sed 1 | Ib | alpha | 1/15 | 10/15** | n.d. |

C3H/HeN mice were injected i.p. with 0.1 ml of rabbit antiserum (diluted to 0.5 ml with PBS) and challenged 4 h later with an $LD_{90}$ dose of log-phase bacteria, diluted into 0.5 ml of Todd-Hewitt broth. The survival data were analyzed by the chi-square test.
*Expression of protein Rib or the alpha protein, the two antigens relevant to these experiments
[†]No. of mice surviving for 4 days/total no. of infected mice
[§]P < 0.001 when compared to the controls receiving anti-alpha serum or normal serum
[ii]n.d. = not determinated
[¶]P < 0.001 when compared to the controls receiving anti-alpha serum
**P < 0.01 when compared to the controls receiving anti-Rib serum The data in Table 2 demonstrate that antiserum to protein Rib protects against lethal infection with BS30, the type III strain from which the protein had been purified. This protection is not unspecific, as shown by the experiments with control sera. The anti-Rib serum also protected against lethal infection with another type III strain, BM110, a member of the high-virulence clone of group B streptococcal strains (Musser et al., *Proc. Natl. Acad. Sci USA* 1989. 86: 4731) In contrast, the anti-Rib serum did not protect against infection with L25one of the type III strains that do not express protein Rib (Table 1). The protective effect of anti-Rib serum was not limited to type III strains, as shown by the experiments with a type II strain expressing protein Rib. As expected, anti-Rib serum did not protect against a type Ib strain expressing the alpha antigen. Taken together, these data strongly suggest that protein Rib acts as a virulence factor in almost all type III strains and in some type II strains, i.e., in most group B streptococcal strains causing invasive infections.

EXAMPLE 8

Cloning of the Rib-Gene and Expression of Protein Rib in *Escherichia Coli*.

Figure 6A:
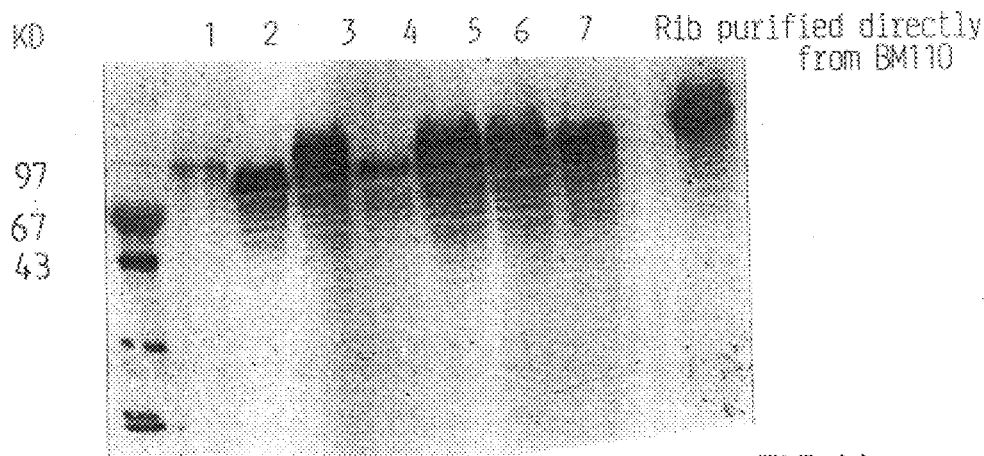
FIGS. 6A, 6B and 6C show the results of cloning of the rib-gene from strain BM110 and expression of protein Rib in *Escherichia coli*. (6A) Western blot analysis of 7 different 1 clones. Incubation with anti-Rib. (6B) Restriction digests of chromosomal DNA from strain BM110. (6C) Restriction digests of the Rib expressing 1-clone 1rib3.
Figure 6B:
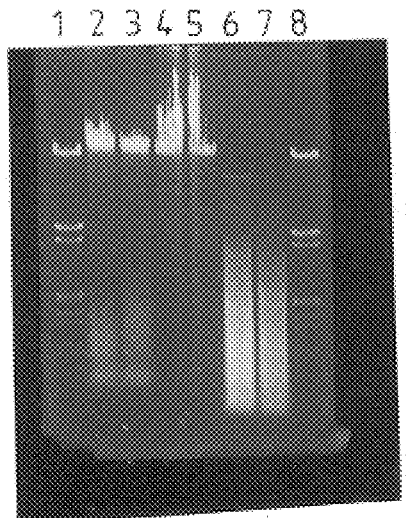
Figure 6C:
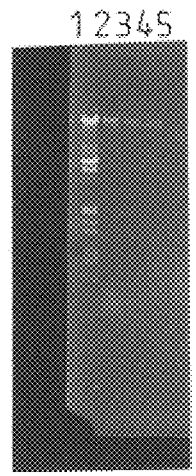

The structural gene for protein Rib was cloned from strain BM110, a serotype III strain which is a member of a high-virulence clone. Protein Rib expressed by this strain (SEQ ID NO:2) and protein Rib expressed by strain BS30 (SEQ ID NO:1) have similar size and $NH_2$-terminal sequence. A library of strain BM110 DNA in bacteriophage lambda was constructed. The bacteria in a 500 ml log-phase Todd-Hewitt culture of the strain BM110 were spun down. The pellet was frozen and thawed 3 times, suspended in 20 ml TE buffer (10 mM Tris, 1 mM EDTA pH 8.0), centrifugated, washed and resuspended in 4 ml of the same buffer. Mutanolysin (Sigma Chemical Co. St Louis, Mo., USA) dissolved to 5000 units/ml in 10 mM potassium phosphate, pH 6.2, was added to the bacterial suspension to give a final concentration of 500 units/ml. Lysozyme (Sigma) was added to a final concentration of 8 mg/ml, and the digestion was allowed to proceed for 3 h at 37° C. The bacterial cells were lysed by addition of 200 ml of 10% SDS and 500 ml Tween lysing mix (2% Tween-20, 50 mM Tris pH 8.0 and 60 mM EDTA), followed by another 200 ml of 10%. SDS. The lysate was treated with proteinase K (Sigma, 100 mg/ml) for 19 h at 50° C., followed by repeated phenol and chloroform extractions. The DNA was precipitated with ethanol, dried in a SpeedVac concentrator (SAVAC) and dissolved in 4.5 ml TE buffer. The DNA was further purified by CsCl density gradient ultracentrifugation and dialyzed against TE buffer. The DNA concentration was then approximately 2.5 mg/ml. This DNA was partially digested with Sau 3AI (Promega), and ligated to Bam HI-cleaved arms of lEMBL 3 (Statagene). The recombinant phage DNA was packaged in vitro using Gigapack II Gold Packaging Extract (Stratagene). The library was plated on the *E. coli* strain LE392 and screened for production of protein Rib with an immuno-blotting technique: plates with about 1000 plaques were covered with a nitrocellulosa membrane and left at 4° C. for 1 h. The membranes were removed, blocked, and incubated in buffer containing rabbit anti-Rib serum, diluted 50-fold. Positive plaques, i.e., those binding rabbit IgG, were detected by addition of peroxidase-labeled protein A (Sigma) (20 mg/ml) and the presence of peroxidase was visualized, using standard techniques. Seven independent Rib expressing lambda clones were isolated. Three of these clones, i.e., lambda Rib1-3, lambda Rib1-5 and lambda Rib1-7, were deposited at Deutsche Sammlung von Microorganismen with deposit numbers DSM 9039, DSM 9040 and DSM 9041 respectively. A preparation of DNA from the lambda Rib1-3 clone having a DNA concentration of about 0.5 mg/ml was also made. Lysates of these seven clones were subjected to Western immunoblot analysis, using anti-Rib serum (see FIG. 6). Several of the clones express protein Rib of the same size as protein Rib isolated directly from strain BM110.

EXAMPLE 9

Isolation and Sequencing of the Rib Protein

Bacterial Strains and Cloning Vectors

The GBS strain BM110 is a serotype III isolate obtained from Dr. S. Mattingly (University of Texas, San Antonio, Tex.) as described above. *Escherichia coli* strain LE 392 (Genofit, Geneva, Switzerland) was used as a host for the cloning vector λEMBL3 (Promega Co., Madison, Wis.). For subcloning, *E. coli* strain XL1-Blue (which is recA1) (Stratagene, La Jolla, Calif.) was used as a host for the cloning vector pGEM7Z(f+) (Promega Co.), and the *E. coli* strain JM103 (Amersham Corp.) was used as a host for the sequencing vectors M13mp18 or M13mp19 (Amersham Corp.). Standard techniques were used for work with *E. coli* and cloning vectors (Sambrook, J., Fritscn, E. F. and Maniatis, T. (1989) Molecular Cloning: A Laboratory Manual, 2nd Ed., Cold Spring Harbor Laboratory Press, Cold Spring Harbor, N.Y.).

Media, Chemicals, and Purified Proteins

GBS was grown in Todd-Hewitt broth, and *E. coli* was grown in LB broth at 37° C. Ampicillin (50 µg/ml) and tetracycline (5 µg/ml) were added when appropriate. Restriction enzymes were purchased from Promega Co., New England Biolabs Inc. (Beverly, Mass.) or Boehringer Mannheim.

The Rib, α, and β proteins were purified from extracts of strains BM110, A909, and SB35, respectively, by a combination of ion exchange and molecular sieve chromatography as described above and in Stålhammer-Carlemalm et al. (1993), followed by a final step of hydroxylapatite chromatography for removal of small amounts of contaminating polysaccharides.

DNA Sequencing and Sequence Analysis

DNA sequences were determined by the dideoxy chain termination method using [α-$^{35}$S]dATP (Amersham Corp.) and Sequenase 2.0 (Amersham Corp.). Recombinant M13amp18 or M13mp19 phage DNA was used as template. M13 universal primer and −40 primer (Amersham Corp.) as well as custom made primers were used. The sequencing reaction products were resolved on 8% polyacrylamide-urea gels. Gels were run at 40 W for 1–4 h on a sequencing unit from Cambridge Electrophoresis Ltd. (Cambridge, UK), fixed in 10% methanol, 10% acetic acid for 15 min, and dried on Watman 3MM papers under vacuum. Computer-assisted analysis of DNA sequences was performed with the GCG software package (Genetics Computer Group (1994)) and the GeneWorks program (IntelliGenetics, Inc., Mountain View, Calif.).

Polymerase Chain Reaction Analysis

The rib gene was amplified from purified DNA in a 50-µl volume using primers with the sequences 5'-TGACTAAAAATGTTCAGAATGGTAG-3' (SEQ ID NO: 7) and 5'-GAAACAGATAATAAACCAACTGATG-3' (SEQ ID NO: 8). Each reaction mixture contained 12.5 pmol of each primer, 0.2 mM dNTPs, 2.5 units AmpliTaq DAN polymerase (Perkin-Elmer) and 1.5 mM MgCl$_2$ in the incubation buffer supplied with the enzyme. PCR amplification was performed by 30 repeated cycles on a programmable thermal controller (PTC-100, Promega Co.) with a thermal step program that included: denaturation at 94° C. for 60 s, annealing at 57° C. for 60 s, and primer extension at 72° C. for 120 s. Amplified material was analyzed on 1.0% agarose gels.

Solid Phase Radioimmunoassay

Microtiter plates (Falcon 3912, Becton Dickinson, Oxnard, Calif.) were coated with purified protein Rib or α by incubation for 16 h with 100 µl of a solution (100 ng/ml) of protein in PBS (0.03 M phosphate, 0.12 M NaCl, pH 7.2). The wells were blocked by washing with VBS (10 mM veronal buffer, 0.15 M NaCl, pH 7.4) supplemented with 0.25% gelatin and 0.25% Tween 20. Rabbit antisera against the Rib and α proteins, obtained as indicated above, were used at dilutions corresponding to 50–60% of maximal binding. The binding between anti-Rib and immobilized Rib, and between anti-α and immobilized α, was inhibited by the addition of purified Rib or α. For these inhibition experiments 100 µl aliquots of antiserum in PBSAT (PBS containing 0.02% NaN$_3$ and 0.05% Tween20) were preincubated for 30 min with various amounts (160 pg to 500 ng) of Rib or α and then added to the wells. After 3 h of incubation the wells were washed three times with PBSAT and the presence of antibodies was analyzed by addition of $^{125}$I-labeled protein G (20,000 cpm in 100 µl/well) and incubation for 2 h. After three washes with PBSAT, the radioactivity of each well was determined in a γ-counter. Non-specific binding (less than 1%) was determined in wells coated with buffer (PBS) alone. All incubations were performed at room temperature.

Other Methods

SDS-PAGE was performed using a Protean II cell (Bio-Rad, Hercules, Calif.). The gels were stained with Coomassie brilliant blue R-250 or transferred by electroblotting to Immobilon filters (Millipore Corp., Molsheim, France) in a Semi-Dry Electroblotter (Ancos, Vig, Denmark). Tricine gels were used for the analysis of peptide fragments (Schägger, H. and von Jagow, G. (1987) Anal. Biochem. 166 368–379). For Western blot analysis, membranes were incubated with antisera as described. Amino-terminal sequence analysis of proteins transferred to ProBlott membranes was performed with a 470A Protein Sequencer (Applied Biosystems, Foster City, Calif.).

EXAMPLE 10

Kit

The components of the present invention may be packaged as a kit. Uses of the kit may be for the detection of antibodies to protein Rib or for the detection of protein Rib, however other uses are possible. Each component of the kit(s) may be individually packaged in its own suitable container. The individual containers may also be labelled in a manner which identifies the contents. Moreover, the individually packaged components may be placed in a larger container capable of holding all desired components. Associated with the kit may be instructions which explain how to use the kit. These instructions may be written on or attached to the kit.

We claim:

1. A purified protein encoded by SEQ ID NO:4 or immunogenic fragment thereof which is resistant to degradation by trypsin and pepsin.

2. A purified protein comprising one or more repeats of SEQ ID NO:6, wherein said protein confers immunity to Group B streptococcus type III organisms expressing Rib protein.

3. A purified protein of claim 2 wherein said one or more repeats of SEQ ID NO:6 are joined by an acid labile linkage.

4. A purified protein of claim 2 wherein said one or more repeats of SEQ ID NO:6 are joined by an Asp-Pro linkage.

5. A pharmaceutical composition comprising the protein of claims 1 or 2 and a pharmaceutically acceptable carrier therefor.

6. A vaccine comprising the protein of claim 2.

7. A method of inducing an immune response in an animal against Group B Streptococcus comprising immunizing said animal with the protein as defined in claim 1 or 2.

8. The method of claim 7 wherein said animal is a human.

9. Purified antibodies specific for protein Rib or immunogenic fragments thereof from Group B streptococcus, type III as defined in claim 1.

10. Purified antibodies specific for the protein as defined in claim 2.

11. A reagent kit for detection of antibodies to protein Rib comprising protein Rib or immunogenic fragments thereof from Group B streptococcus, type III as defined in claim 1.

12. A reagent kit for detection of protein Rib comprising antibodies specific to the protein as defined in claim 1.

13. A reagent kit as defined in claim 12, further comprising one or more components selected from the group consisting of protein Rib, and immunogenic fragments thereof as a standard against which the detected Rib protein is compared.

14. A reagent kit for detection of antibodies to the protein as defined in claim 2.

15. A reagent kit for detection of protein Rib comprising antibodies specific to the protein as defined in claim 2.

16. A reagent kit as defined in claim 15, further comprising a protein comprising one or more repeats of SEQ ID NO:6 as a standard against which the detected Rib protein is compared.

17. A purified fusion protein comprising the protein or immunogenic fragment of claim 1.

* * * * *